(12) United States Patent
Muppireddy et al.

(10) Patent No.: US 11,701,350 B2
(45) Date of Patent: Jul. 18, 2023

(54) DEXTROMETHORPHAN EXTENDED RELEASE PHARMACEUTICAL COMPOSITION

(71) Applicant: L. Perrigo Company, Allegan, MI (US)

(72) Inventors: Kiran Kumar Muppireddy, Portage, MI (US); Inderdeep Singh Bhatia, Kalamazoo, MI (US); Eric Cristopher Pattok, Grand Rapids, MI (US); Carlos O. Paz, Fairview, NJ (US); Bruce Duane Johnson, Byron Center, MI (US); Lisa Kay Lupton, Kalamazoo, MI (US)

(73) Assignee: L. PERRIGO COMPANY, Allegan, MI (US)

( * ) Notice: Subject to any disclaimer, the term of this patent is extended or adjusted under 35 U.S.C. 154(b) by 169 days.

(21) Appl. No.: 16/935,661

(22) Filed: Jul. 22, 2020

(65) Prior Publication Data

US 2021/0023073 A1    Jan. 28, 2021

Related U.S. Application Data

(60) Provisional application No. 62/876,934, filed on Jul. 22, 2019.

(51) Int. Cl.
*A61K 31/485* (2006.01)
*A61K 9/20* (2006.01)
*A61K 9/28* (2006.01)

(52) U.S. Cl.
CPC .......... *A61K 31/485* (2013.01); *A61K 9/2009* (2013.01); *A61K 9/2013* (2013.01); *A61K 9/2027* (2013.01); *A61K 9/2031* (2013.01); *A61K 9/2054* (2013.01); *A61K 9/2826* (2013.01); *A61K 9/2853* (2013.01)

(58) Field of Classification Search
None
See application file for complete search history.

(56) References Cited

U.S. PATENT DOCUMENTS 5,980,882  A    11/1999  Eichman
7,014,867  B2   3/2006   Fanara et al.
9,265,760  B2   2/2016   Hartman et al.
(Continued)

OTHER PUBLICATIONS

Meyyanathan et al. Formulation and Evaluation of Dextromethorphan Hydrobromide Sustained Release Tablets. Drug Delivery, 15:429-435. (Year: 2008).*

(Continued)

*Primary Examiner* — Lakshmi S Channavajjala
(74) *Attorney, Agent, or Firm* — Honigman LLP; Christopher C. Forbes

(57) ABSTRACT

The invention is directed to pharmaceutical compositions comprising dextromethorphan and methods of use thereof. Formulations of the present invention include dextromethorphan or a pharmaceutically acceptable salt thereof in a sustained release formulation comprising a controlled release agent. Formulations of the present invention include a core tablet, optionally an active coating and, optionally a film coating. The pharmaceutical compositions may be used as an antitussive, and the invention further relates to the treatment of cough in a patient in need thereof.

13 Claims, 9 Drawing Sheets

(56) References Cited

U.S. PATENT DOCUMENTS

| | | | |
|---|---|---|---|
| 9,339,499 B2 | 5/2016 | Hartman et al. | |
| 9,872,836 B2* | 1/2018 | Wright | A61K 9/2853 |
| 9,962,342 B1 | 5/2018 | Hung et al. | |
| 2005/0276852 A1* | 12/2005 | Davis | A61P 11/10 |
| | | | 424/468 |
| 2013/0022646 A1* | 1/2013 | Rudnic | A61K 9/5026 |
| | | | 514/282 |

OTHER PUBLICATIONS

Reynolds et al Investigation of the Effect of Tablet Surface Area/ Volume on Drug Release from Hydroxypropylmethylcellulose Controlled-Release Matrix Tablets. Drug development and Industrial Pharmacy, 28(4), 457-466. (Year: 2002).*

* cited by examiner

DEXTROMETHORPHAN EXTENDED RELEASE PHARMACEUTICAL COMPOSITION

FIELD OF THE INVENTION

The invention is directed to extended release pharmaceutical compositions comprising dextromethorphan and methods of use thereof. Formulations of the present invention include dextromethorphan in a sustained release formulation and a coating. The pharmaceutical compositions may be used as an antitussive.

BACKGROUND OF THE INVENTION

Dextromethorphan is a known antitussive. Dextromethorphan hydrobromide is typically marketed in a syrup product form or solid dosage forms as an immediate release dosage form. Controlled release formulations containing dextromethorphan hydrobromide are also on the market. A dextromethorphan polistirex extended release suspension is marketed under the trade name Delsym®, which requires a complex manufacturing process. The current marketed sustained release suspension is a resin-based complex with a dissolution profile showing incomplete release of about 60% in 12 hours in 900 mL, 0.1 N HCl, USP Apparatus II, 75 rpm.

A further extended release dextromethorphan hydrobromide and guaifenesin product is marketed as Mucinex® DM. Current solid dosage forms of extended release formulations may be difficult for consumers suffering from cough symptoms to swallow. For example, Mucinex® DM is marketed in large tablet sizes (volume of about 0.07693 in$^3$, surface area of about 1.01675 in$^2$ and surface area to volume ratio of about 13.2 in that may be difficult to swallow. Manufacturers and consumers also prefer a smooth coating on solid formulations. Therefore, a need exists for an extended release tablet formulation of dextromethorphan that is easy to swallow and has similar in-vivo performance in comparison to products currently on the market.

SUMMARY OF THE INVENTION

The present invention includes pharmaceutical compositions and methods of treating cough using extended release pharmaceutical compositions comprising dextromethorphan or pharmaceutically acceptable salts thereof. One aspect of the invention comprises an extended release pharmaceutical composition comprising a sustained release formulation, wherein the sustained release formulation comprises dextromethorphan or a pharmaceutically acceptable salt thereof and a controlled release agent or agents. In another aspect of the invention, the tablet volume does not exceed 0.0183 in$^3$, surface area does not exceed 0.395 in$^2$, and surface area to volume ratio is between 19.4 in$^{-1}$ and 31.0 in$^{-1}$. This provides an advantage over the currently marketed tablet products, as the tablet size is much smaller and allows for easier swallowing. Another advantage of the current invention is that it uses a simple manufacturing process and does not include any complexation agents, while achieving the same therapeutic effect. In another aspect of the invention, the tablet includes an active coating comprising dextromethorphan, a film former, a crystal growth inhibitor, a surfactant, and/or a plasticizer. In some other aspects, the invention has a favorable dissolution profile. In some other aspects, the invention has a flavoring and/or cooling agent in the coating, which can provide the patient suffering from cough with a soothing effect.

In another aspect of the invention, pharmaceutical compositions comprising dextromethorphan may be used to reduce cough in a subject in need thereof.

DETAILED DESCRIPTION OF THE INVENTION

Definitions

Figure 1:
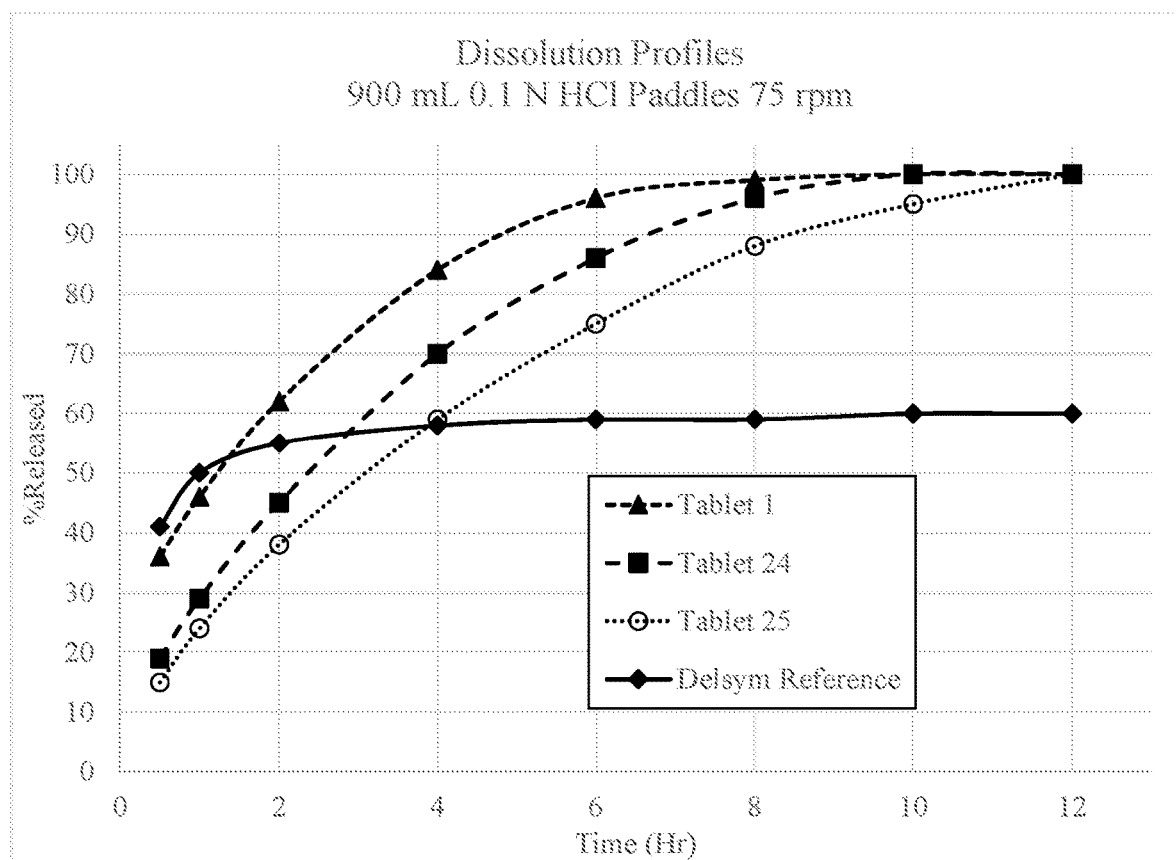
FIG. 1 is a line graph providing the dissolution profile of tablet formulations 1, 24, and 25 of the present invention compared to the reference listed drug suspension product, Delsym®.

As used herein, the term "Sustained release formulation" may be used to describe a formulation for release of an active ingredient at such a rate that blood levels of the active ingredient are maintained within the therapeutic range over an extended period of time, for example, 12 to 24 hours.

As used herein, the term "treat" or "treating" means to give medical attention with the intent of curing, eliminating, or reducing the symptoms of a disease or condition.

As used herein the term "about" when preceding a numerical value, indicates that the numerical value can be ±5% of the total value indicated; for example when a measured quantity disclosed herein is "about 100%", the actual quantity could be from 95% to 105%. Unless specified otherwise, when the term "about" precedes a list of more than one numerical value, the term "about" is meant to be applied to all numerical values in the list.

As used herein, the term "cooling agent" relates to chemical compounds that are generally employed as excipients in pharmaceutical compositions to provide a cooling sensation when the pharmaceutical composition is consumed. Cooling agents, used in the pharmaceutical compositions as excipients provide a cooling sensation to the mouth, throat and gastrointestinal tract. Examples of cooling agents include, but are not limited to thymol, menthol, menthyl lactate, sorbitol, xylitol, erythritol, lactitol, mannitol, cooling agent WS-23 (butanamide, N-2,3-trimethyl-2-(1-methylethyl)-), cooling agent WS-3 (cyclohexanecarboxamide, N-ethyl-5-methyl-2-(1-methylethyl)-), cooling agent WS-5 (N-(ethoxycarbonylmethyl)-3-p-menthanecarboxamide), cooling agent WS-12 ((1R,2S,5R)—N-(4-methoxyphenyl)-5-methyl-2-(1-methylethyl)cyclohexanecarboxamide), and Symcool® Extra WSE-500 (proprietary blend from Symrise).

EMBODIMENTS OF THE INVENTION

The pharmaceutical compositions of the present invention provide a solid dosage form comprising a sustained release formulation. Compositions of the present invention may be used to reduce cough in a patient in need thereof.

In some embodiments, pharmaceutical compositions of the present invention may comprise a sustained release formulation. In further embodiments, pharmaceutical compositions of the present invention may comprise a coating.

In some embodiments, the sustained release formulation may be a tablet. In some embodiments, the sustained release formulation may comprise dextromethorphan or a pharmaceutically acceptable salt thereof. In some embodiments, the sustained release formulation comprises dextromethorphan HBr.

In some embodiments, the sustained release formulation may comprise dextromethorphan or a pharmaceutically acceptable salt thereof. In some embodiments, the sustained release formulation comprises dextromethorphan or a pharmaceutically acceptable salt thereof in an amount of from about 10% to about 60% by weight of the composition. In some embodiments, the sustained release formulation comprises dextromethorphan HBr in an amount of from about 10% to about 60% by weight of the composition. In some further embodiments, the sustained release formulation comprises dextromethorphan HBr in an amount of from about 10% to about 30% by weight of the composition.

In some embodiments, the sustained release formulation may comprise a controlled release agent. Controlled release agents may be used in pharmaceutical compositions of the present invention to release dextromethorphan or a pharmaceutically acceptable salt thereof at a predetermined rate to maintain a constant drug concentration for a predetermined amount of time. In some embodiments, the controlled release agent is a polymer. Polymers suitable for use in controlled release formulations include: one or more natural, partially or totally synthetic hydrophilic gums such as acacia, gum tragacanth, locust bean gum, guar gum, or karaya gum; cellulose ethers such as methylcellulose, hydroxomethylcellulose, hydroxypropyl methylcellulose (HPMC), hydroxypropyl cellulose, hydroxyethylcellulose, carboxymethylcellulose; proteinaceous substances such as agar, pectin, carrageen, and alginates; and other polymers such as carboxypolymethylene, gelatin, casein, zein, bentonite, magnesium aluminum silicate, polysaccharides, modified starch derivatives, ethyl cellulose, methacrylic acid-ethyl acrylate copolymers.

Polymers suitable for use as controlled release agents in the formulations described herein can gel and dissolve slowly in aqueous media thereby allowing the dextromethorphan to diffuse from the gel matrix. When the gel reaches the stomach and intestines, it dissolves in controlled quantities, where the dextromethorphan is fairly absorbable, to allow sustained release of dextromethorphan throughout the digestive tract.

In one embodiment, the controlled release agent is a cellulose ether. In another embodiment, the controlled release agent is a functionalized cellulose ether. In a further embodiment, the cellulose ether is functionalized with methyl groups and/or hydroxypropyl groups. In yet a further embodiment, the cellulose ether is functionalized with both methyl and hydroxypropyl groups, e.g. hydroxypropylmethyl cellulose or hypromellose. As used herein, "hypromellose" is synonymous and can be used interchangeably with "hydroxypropyl methylcellulose". In some embodiments, specific physical properties of hypromellose are achieved by varying the length of the base cellulose ether polymer and/or the ratios of methyl substitution vs. hydroxypropyl substitution.

As used herein, the term "viscosity" refers to a quantity expressing the magnitude of internal friction, as measured by the force per unit area resisting a flow in which parallel layers unit distance apart have unit speed relative to one another. Unless indicated otherwise, the viscosity of a polymer is reported herein as units of mPa·s (millipascal seconds), wherein the polymer has a concentration of 2 wt % in water.

In one specific embodiment, the hydroxypropyl methylcellulose has
1) an apparent viscosity of from about 2,663 to about 4,970 mPa·s at 2 wt % in water;
2) a methyl substitution between about 22.0% and 24.0%; and
3) a hydroxypropyl substitution between about 7.5% and 9.5%; and In another specific embodiment, the hydroxypropyl methylcellulose has
1) an apparent viscosity of from about 13,275 to about 24,780 mPa·s at 2 wt % in water;
2) a methyl substitution between about 22.0% and 24.0%; and
3) a hydroxypropyl substitution between about 8.5% and 10.5%.

In yet another specific embodiment, the hydroxypropyl methylcellulose has
1) an apparent viscosity range of about 2.4-7 mPa·s at 2 wt % in water;
2) a methyl substitution range of about 28.0%-30.0%; and
3) a hydroxypropyl substitution range between about 7.0%-12.0%.

As used herein, "METHOCEL" is a trademark of The Dow Chemical Company for a line of cellulose ether products. An initial letter in this trademark identifies the type of cellulose ether, for example "K" identifies one type of hypromellose product having a specific range of methyl vs. hydroxypropyl substitution ratio, while "E" identifies another type having a different range of methyl vs. hydroxypropyl substitution ratio. The number that follows identifies the viscosity in millipascal-seconds (mPa·s) measured at 2% concentration in water at 20° C. In designating viscosity, the letter "M" is used to represent 1000. The suffix "CR"

denotes a controlled-release grade that is manufactured to have an especially fine particle size, where greater than 90% of the particles pass through 100 mesh, in the K type of hypromellose. The suffix "LV" denotes a low viscosity grade that is manufactured to have a low viscosity when dissolved in water. Specific types of METHOCEL' are detailed below.

In some embodiments, the sustained release formulation comprises hypromellose having a ratio of methyl vs. hydroxypropyl substitution that corresponds to METHOCEL' substitution type E or K. In another embodiment, the sustained release formulation comprises hypromellose having a viscosity in the range of 100 to 50,000 mPa·s measured at 2% concentration in water at 20° C. In some embodiments of a sustained release formulation, the hydrophillic polymer acts as controlled release agent. In some other embodiments of a sustained release formulation, the hydrophillic polymer acts as a low viscosity excipient.

In one preferred embodiment of a sustained release formulation the hydrophilic polymer is a type of hypromellose sold under the trademark METHOCEL™, such as METHOCEL™ K4MCR, METHOCEL™ K15MCR, and mixtures thereof.

As used herein, "METHOCEL™ K4MCR" refers to hypromellose sold by The Dow Chemical Company under the trademark "METHOCEL™ K4MCR" and is a cellulose core structure with the following properties: apparent viscosity range: 2,663-4,970 mPa·s, methyl substitution: 22.0%-24.0% (inclusive); hydroxypropyl substitution: 7.5-9.5% (inclusive). In one embodiment, hypromellose sold under the trademark "METHOCEL™ K4MCR" acts as a controlled release agent.

As used herein, "METHOCEL™ K15MCR" refers to hypromellose sold by The Dow Chemical Company under the trademark "METHOCEL™ K15MCR" and is a cellulose core structure with the following properties: apparent viscosity range: 13,275-24,780 mPa·s, methyl substitution: 22.0%-24.0% (inclusive) and hydroxypropyl substitution: 8.5-10.5% (inclusive). In one embodiment, hypromellose sold under the trademark "METHOCEL™ K15MCR" acts as a controlled release agent.

As used herein, "METHOCEL™ E3LV" refers to hypromellose sold by The Dow Chemical Company under the trademark "METHOCEL™ E3LV" and is a cellulose core structure with the following properties: apparent viscosity range: 2.4-3.6 mPa·s, methyl substitution: 28.0%-30.0% (inclusive) and hydroxypropyl substitution: 7.0%-12.0% (inclusive). In one embodiment, hypromellose sold under the trademark "METHOCEL™ E3LV" acts as a low viscosity agent.

As used herein, "METHOCEL™ A4M" refers to methylcellulose (no hydroxypropyl substitution) sold by The Dow Chemical Company under the trademark "METHOCEL™ A4M" and is a cellulose core structure with an apparent viscosity range of 3,000-5,500 mPa·s. In one embodiment, hypromellose sold under the trademark "METHOCEL™ A4M" acts as a high viscosity agent.

In some embodiments, the sustained release formulation may comprise a controlled release agent in an amount of from about 0 to about 50% by weight of the composition. In some embodiments, the controlled release agent comprises HPMC having an apparent viscosity of from about 2,663 to about 4,970 mPa·s at 2 wt % in water (e.g. METHOCEL™ K4MCR) in an amount of from about 0% to about 50% by weight (e.g. about 5% to about 45%; about 5% to about 35%, or about 8% to about 34%) of the composition. In some embodiments, the controlled release agent comprises HPMC having an apparent viscosity of from about 13,275 to about 24,780 mPa·s at 2 wt % in water (e.g. METHOCEL™ K15MCR) in an amount of from about 0% to about 40% by weight (e.g. 0% to about 30%, 0% to about 25%, or 8% to about 25%) of the composition.

In some embodiments, the sustained release formulation may comprise a water soluble and/or insoluble diluent. As used herein, the term "diluent" (also referred to as a "filler" or "thinner") refers to any pharmaceutically acceptable diluting agent that may be used in the practice of the invention. Examples of diluents that may be used in the present invention are selected from, but not limited to, lactose, e.g. lactose monohydrate; celluloses, e.g. microcrystalline cellulose; calcium phosphates, e.g. dicalcium phosphate; starches; sugar alcohols, e.g. mannitol, sorbitol, and xylitol; sugars, e.g. sucrose; or any combination thereof. In some embodiments, the sustained release formulation comprises a diluent in an amount of from about 0% to about 80% by weight (e.g. about 10% to about 70%, about 20% to about 65%, about 30% to about 60%, or about 33% to about 57%) of the composition. In some embodiments, the diluent comprises lactose monohydrate in an amount of from about 0% to about 60% by weight (e.g. about 10% to about 50%, or about 10% to about 45%, or about 14% to about 41%) of the composition. In some embodiments, the diluent comprises microcrystalline cellulose in an amount of from about 0% to about 40% by weight (e.g. 0% to about 35%, 0% to about 31%, about 10% to about 35%, or about 13% to about 31%) of the composition. In some embodiments, the diluent is a mixture of lactose monohydrate and microcrystalline cellulose.

In some embodiments, the sustained release formulation may comprise a glidant. As used herein, "glidant" refers to any pharmaceutically acceptable substance that is added to a powder to improve its flowability. In some embodiments, the glidant may be a fumed silica, colloidal silica, precipitated silica, talc, or any combination thereof. In some embodiments, the glidant may be CAB-O-SIL® M-5. In some embodiments, the sustained release formulation may comprise a glidant in an amount of from about 0% to about 1% by weight (e.g. from about 0.3% to about 0.6% or from about 0.30% to about 0.52%) of the composition. In some embodiments, the sustained release formulation may comprise a glidant in an amount of from about 0% to about 1% by weight of the composition. In some embodiments, the sustained release formulation may comprise a glidant in an amount of from about 0.4% to about 0.5% by weight of the composition.

As used herein, "CAB-O-SIL® M-5" refers to fumed silica sold by The Cabot Corporation under the trademark "CAB-O-SIL® M-5".

In some embodiments, the sustained release formulation may comprise a lubricant. As used herein, a "lubricant" is an excipient that is added to pharmaceutical compositions that are pressed into tablets, and aids in compaction of powder and/or granules into tablets and ejection of a tablet of a pharmaceutical composition from a die press. In some embodiments, the lubricant may be magnesium stearate, stearic acid (stearin), hydrogenated castor oil, sodium stearyl fumarate, or any combination thereof. In some embodiments, the sustained release formulation may comprise a lubricant in an amount of from about 0% by weight to about 2% by weight (e.g. from about 0.2% to about 1%, from about 0.3% to about 0.8%, or from about 0.33% to about 0.77%) of the composition. In some embodiments, the sustained release formulation may comprise a lubricant in an amount of 0.35%, 0.49%, 0.50%, 0.67%, 0.69%, 0.70%, 0.71%, 0.72%, 0.73%, or 0.75% by weight of the composition.

In some embodiments, the pharmaceutical composition may comprise a single layer matrix, bi-layer tablet containing an immediate release portion, or a coating containing immediate release component. In some embodiments, the coating may comprise a coating agent. As used herein "coating agent" refers to any pharmaceutically acceptable, natural or synthetic substance used to film coat the dosage carrier with a thin layer of polymeric material that protects the API from moisture, light or the acidic environment of the stomach, provides a slippery surface for the ease of swallowing, and/or masks the bitter taste of an active pharmaceutical ingredients. In some embodiments, the coating agent may be commercially available as OPADRY®. In some embodiments, the coating may comprise a coating agent in an amount of from about 0% to about 5% by weight (e.g. from about 0.45% to about 3.0%) of the composition. In some embodiments, the coating may comprise a coating agent in an amount of from about 0% to about 1% (e.g. from about 0.3% to about 0.8% or from about 0.45% to about 0.55%) by weight of the composition. In some embodiments, the coating may comprise a coating agent in an amount of from about 2.5% to about 3.5% by weight (e.g. from about 2.70% to about 3.20% or from about 2.80% to about 3.00%) of the composition.

As used herein, "OPADRY® ORANGE" refers to a tablet coating comprising Polydextrose, HPMC 2910/Hypromellose, FD&C Yellow #6/sunset yellow, Macrogol/PEG 400, Talc, Mica-based pearlescent pigment and Titanium dioxide, sold by Colorcon Inc.

As used herein, "OPADRY® CLEAR" refers to a tablet coating comprising HPMC 2910/Hypromellose and Macrogol/PEG MW 400, sold by Colorcon Inc.

In some embodiments, the coating may comprise a flavoring agent, a cooling agent, a sweetener, or a salivation agent.

In some embodiments, pharmaceutical compositions of the present invention reduce the growth of crystals of dextromethorphan or pharmaceutically acceptable salts thereof. It is known to those having skill in the art that dextromethorphan HBr is highly crystalline, and can form crystals during the formulation processes. For example, a solution comprising dextromethorphan HBr and METHOCEL' E3 LV formed a precipitate at room temperature during coating process that prevented deposition of the API on the tablets. It is necessary for the active pharmaceutical ingredient to remain dissolved in the coating solution throughout the coating process. Described herein are specific excipients and processing parameters used to prevent dextromethorphan, the active pharmaceutical ingredient, from precipitating out of solution during the formulation process.

In some embodiments, pharmaceutical compositions of the present invention provide a tablet formulation having a smooth surface. The importance of having a relatively smooth surface on the tablets after coating is known to those having skill in the art. One exemplary reason for this is because manufacturers and consumers prefer a smooth appearance on their medicine. Dextromethorphan is prone to precipitation during active coating which may give pharmaceutical compositions a rough appearance. Described herein are specific excipients and processing parameters used to prevent precipitation of dextromethorphan, the active pharmaceutical ingredient, during the coating process to provide a smooth surface on the tablet formulation.

During the development of the active coating system, several small scale studies were conducted to select a formulation composition. During production of Tablet 2, sedimentation of active pharmaceutical ingredient in the coating solution lines was observed. Therefore, the addition of a crystal growth inhibitor (Povidone) and plasticizer (Polyethylene Glycol) were evaluated (Tablet 3). These excipients allowed for better processability compared to the Tablet 2 batch, however settling in the periphery of tubing was eventually observed during the coating run and the resulting tablets had poor appearance. The addition of a surfactant (SLS) to improve solubility was further evaluated (Tablet 4). No processability or tablet appearance issues were encountered during this coating trial. The addition of a film-former (Kolllicoat IR) was also evaluated (Tablet 5) to further improve the tablet processability and appearance upon larger scale coating trials. METHOCEL™ E3 LV was also evaluated as a film-former in the active coating composition (Tablet 1 and Tablet 2), which resulted in acceptable processability and tablet appearance at pilot scale.

Pharmaceutical compositions of the present invention may be used to treat cough symptoms. In some embodiments, pharmaceutical compositions of the present invention may reduce cough in a subject in need thereof.

In some embodiments, pharmaceutical compositions of the present invention are tablets. In some embodiments, the pharmaceutical composition may comprise dextromethorphan HBr in an amount of about 30 mg. In some embodiments, the pharmaceutical composition may comprise dextromethorphan HBr in an amount of about 60 mg.

In one aspect, the invention includes a sustained release pharmaceutical composition comprising:
   a. dextromethorphan or a pharmaceutically acceptable salt thereof in an amount of from about 10% to about 60% by weight of the composition;
   b. a controlled release agent in an amount of from about 10% to about 55% by weight of the composition; and
   c. a water soluble and/or insoluble diluent in an amount of from about 10% to about 80% by weight of the composition.

In one embodiment, the invention includes a sustained release pharmaceutical tablet composition comprising:
   a. dextromethorphan or a pharmaceutically acceptable salt thereof in an amount of from about 20% to about 35% by weight of the composition;
   b. a controlled release agent in an amount of from about 10% to about 55% by weight of the composition; and
   c. a water soluble and/or insoluble diluent in an amount of from about 10% to about 80% by weight of the composition.

In one embodiment, the composition includes dextromethorphan or a pharmaceutically acceptable salt thereof in an amount of from about 20% to about 35% by weight of the composition. In one embodiment, the composition includes dextromethorphan or a pharmaceutically acceptable salt thereof in an amount of from about 25% to about 30% by weight of the composition. In one embodiment, the composition includes dextromethorphan or a pharmaceutically acceptable salt thereof in an amount selected from 27.39%, 28.04%, 27.65%, 27.49%, 27.37%, 27.88%, 28.17%, 25.75%, 25.00%, 26.67%, 12.50%, 17.44%, and 18.40% by weight of the composition. In a further embodiment, the composition includes dextromethorphan or a pharmaceutically acceptable salt thereof in an amount of 25.00% by weight of the composition.

In one embodiment, the tablet contains about 30 mg of dextromethorphan HBr. In another embodiment, the tablet has a mass of from about 110 mg to about 250 mg. In a further embodiment, the tablet contains about 30 mg of dextromethorphan HBr and has a mass of from about 110 mg to about 250 mg. In another embodiment, the tablet contains about 30 mg of dextromethorphan HBr and has a mass of from about 115 mg to about 125 mg. In still a further embodiment, the tablet contains about 30 mg of dextromethorphan HBr and has a mass that is selected from about 120 mg, about 172 mg, and about 240 mg.

In one embodiment, the tablet contains about 60 mg of dextromethorphan HBr. In another embodiment, the tablet has a mass of from about 200 mg to about 335 mg. In a further embodiment, the tablet contains about 60 mg of dextromethorphan HBr and has a mass of from about 200 mg to about 335 mg. In another embodiment, the tablet contains about 60 mg of dextromethorphan HBr and has a mass of from about 210 mg to about 242 mg. In still a further embodiment, the tablet contains about 60 mg of dextromethorphan HBr and has a mass that is selected from about 219 mg, 214 mg, 217 mg, 218 mg, 215 mg, 213 mg, 233 mg, 240 mg, 225 mg, and 326 mg.

In one embodiment, the tablet has a volume of from about 0.0063 in³ to about 0.0183 in³.

In one embodiment, the tablet has a surface area of from about 0.194 in² to about 0.395 in².

In one embodiment, the tablet has a surface area to volume ratio of from about 19.4 in⁻¹ to about 31.0 in⁻¹.

In another embodiment, the sustained release pharmaceutical composition comprises dextromethorphan HBr.

In one embodiment, the sustained release pharmaceutical composition comprises from about 15% to about 55% by weight of the composition of the controlled release agent. In one embodiment, the controlled release agent is a cellulose ether. In another embodiment, the controlled release agent is a functionalized cellulose ether. In a further embodiment, the cellulose ether is functionalized with methyl groups and/or hydroxypropyl groups. In yet a further embodiment, the cellulose ether is functionalized with both methyl and hydroxypropyl groups, e.g. hydroxypropylmethyl cellulose or hypromellose or METHOCEL™. In some embodiments, specific physical properties of hypromellose are achieved by selecting specific ratios of methyl substitution vs. hydroxypropyl substitution.

In one embodiment, the controlled release agent is selected from the group consisting of METHOCEL™ K4MCR, METHOCEL™ K15MCR, and combinations thereof. In still a further embodiment, the controlled release agent is a combination of METHOCEL™ K4MCR and METHOCEL™ K15MCR.

In one embodiment, the composition comprises from about 5% to about 40% by weight of the composition of METHOCEL™ K4MCR. In another embodiment, the composition comprises from about 5% to about 30% by weight of the composition of METHOCEL™ K15MCR. In another embodiment, the composition comprises from about 8% to about 20% by weight of the composition of METHOCEL™ K4MCR. In a further embodiment, the composition comprises from about 9% to about 20% by weight of the composition of METHOCEL™ K15MCR. In a further embodiment, the weight percent of METHOCEL™ K4MCR in the composition is selected from 8.33%, 8.58%, 8.89%, 9.12%, 9.13%, 9.17%, 9.22%, 9.29%, 9.39%, 9.52%, 12.27%, 14.08%, 15.89%, 16.67%, 17.17%, 17.44%, 17.78%, 18.40%, 18.78%, 22.39%, 25.00%, 27.50%, 33.33% or 33.91% and the weight percent of METHOCEL™ K15MCR in the composition is selected from 0%, 8.33%, 9.12%, 9.13%, 9.17%, 9.29%, 9.39%, 9.52%, 12.27%, 12.50%, 12.88%, 13.33%, 14.08%, 15.67%, 15.89%, 16.67%, 17.17%, 17.44%, 17.78%, 18.40%, 18.78% or 23.01%.

In a further embodiment, the weight percent of METHOCEL™ K4MCR in the composition is 16.67%, and the weight percent of METHOCEL™ K15MCR in the composition is 16.67%. In another further embodiment, the weight percent of METHOCEL™ K4MCR in the composition is 8.33%, and the weight percent of METHOCEL™ K15MCR in the composition is 16.67%. In another further embodiment, the weight percent of METHOCEL™ K4MCR in the composition is 9.13%, and the weight percent of METHOCEL™ K15MCR in the composition is 9.13%. In another further embodiment, the weight percent of METHOCEL™ K4MCR in the composition is 33.00%, and the weight percent of METHOCEL™ K15MCR in the composition is 0%. In another further embodiment, the weight percent of METHOCEL™ K4MCR in the composition is 25.0%, and the weight percent of METHOCEL™ K15MCR in the composition is 8.33%. In another further embodiment, the weight percent of METHOCEL™ K4MCR in the composition is 17.78%, and the weight percent of METHOCEL™ K15MCR in the composition is 17.78%. In another further embodiment, the weight percent of METHOCEL™ K4MCR in the composition is 8.89%, and the weight percent of METHOCEL™ K15MCR in the composition is 13.33%. In another further embodiment, the weight percent of METHOCEL™ K4MCR in the composition is 9.39%, and the weight percent of METHOCEL™ K15MCR in the composition is 14.08%. In another further embodiment, the weight percent of METHOCEL™ K4MCR in the composition is 8.58%, and the weight percent of METHOCEL™ K15MCR in the composition is 12.88%. In another further embodiment, the weight percent of METHOCEL™ K4MCR in the composition is 17.17%, and the weight percent of METHOCEL™ K15MCR in the composition is 17.17%. In another further embodiment, the weight percent of METHOCEL™ K4MCR in the composition is 18.78%, and the weight percent of METHOCEL™ K15MCR in the composition is 18.78%. In another further embodiment, the weight percent of METHOCEL™ K4MCR in the composition is 14.08%, and the weight percent of METHOCEL™ K15MCR in the composition is 18.78%. In another further embodiment, the weight percent of METHOCEL™ K4MCR in the composition is 9.39%, and the weight percent of METHOCEL™ K15MCR in the composition is 18.78%. In another further embodiment, the weight percent of METHOCEL™ K4MCR in the composition is 9.12%, and the weight percent of METHOCEL™ K15MCR in the composition is 9.12%. In another further embodiment, the weight percent of METHOCEL™ K4MCR in the composition is 9.13%, and the weight percent of METHOCEL™ K15MCR in the composition is 9.13%. In another further embodiment, the weight percent of METHOCEL™ K4MCR in the composition is 9.17%, and the weight percent of METHOCEL™ K15MCR in the composition is 9.17%. In another further embodiment, the weight percent of METHOCEL™ K4MCR in the composition is 9.29%, and the weight percent of METHOCEL™ K15MCR in the composition is 9.29%. In another further embodiment, the weight percent of METHOCEL™ K4MCR in the composition is 9.39%, and the weight percent of METHOCEL™ K15MCR in the composition is 9.39%. In another further embodiment, the weight percent of METHOCEL™ K4MCR in the composition is 9.52%, and the weight percent of METHOCEL™ K15MCR in the composition is 9.52%. In another further embodiment, the weight percent of METHOCEL™ K4MCR in the composition is 9.22%, and the weight percent of METHOCEL™ K15MCR in the composition is 15.67%. In another further embodiment, the weight percent of METHOCEL™ K4MCR in the composition is 15.89%, and the weight percent of METHOCEL™ K15MCR in the composition is 15.89%. In another further embodiment, the weight percent of METHOCEL™ K4MCR in the composition is 8.33%, and the weight percent of METHOCEL™ K15MCR in the composition is 12.50%. In another further embodiment, the weight percent of METHOCEL™ K4MCR in the composition is 12.27%, and the weight percent of METHOCEL™ K15MCR in the composition is 12.27%. In another further embodiment, the weight percent of METHOCEL™ K4MCR in the composition is 17.44%, and the weight percent of METHOCEL™ K15MCR in the composition is 17.44%. In another further embodiment, the weight percent of METHOCEL™ K4MCR in the composition is 27.50%, and the weight percent of METHOCEL™ K15MCR in the composition is 0%. In another further embodiment, the weight percent of METHOCEL™ K4MCR in the composition is 18.40%, and the weight percent of METHOCEL™ K15MCR in the composition is 18.40%. In another further embodiment, the weight percent of METHOCEL™ K4MCR in the composition is 22.39%, and the weight percent of METHOCEL™ K15MCR in the composition is 23.01%. In another further embodiment, the weight percent of METHOCEL™ K4MCR in the composition is 33.91%, and the weight percent of METHOCEL™ K15MCR in the composition is 0%.

In one embodiment, the composition comprises from about 10% to about 60% by weight of the composition of a water soluble and/or insoluble diluent. In another embodiment of this aspect, the composition comprises from about 25% to about 60% by weight of the composition of a water insoluble and/or insoluble diluent.

In one embodiment, the water soluble and/or insoluble diluent is selected from the group consisting of lactose monohydrate, microcrystalline cellulose, or combinations thereof. In a further embodiment, the water soluble and/or insoluble diluent is a combination of lactose monohydrate and microcrystalline cellulose.

In one embodiment, the composition comprises from about 0% to about 45% by weight of the composition of lactose monohydrate. In another embodiment, the composition comprises from about 0% to about 30% by weight of the composition of microcrystalline cellulose.

In another embodiment of this aspect, the composition further comprises a glidant. In one embodiment, the composition comprises a glidant in an amount of from about 0% to about 1% by weight of the composition. In a further embodiment, the composition comprises a glidant in an amount of from about 0.3% to about 0.6% by weight of the composition.

In one embodiment, the glidant is fumed silica. In a further embodiment, the glidant is CAB-O-SIL® M-5.

In another embodiment of this aspect, the composition further comprises a lubricant. In one embodiment, the composition comprises the lubricant in an amount of from about 0% to about 2% by weight of the composition of a lubricant. In a further embodiment, the composition comprises the lubricant in an amount of from about 0.3% to about 1% by weight of the composition of a lubricant.

In one embodiment, the lubricant is magnesium stearate.

In another embodiment of this aspect, the composition further comprises a coating. In one embodiment, the coating comprises a coating agent. In another embodiment, the coating comprises the coating agent in an amount of from about 0% to about 5% by weight of the composition. In a further embodiment, the coating comprises the coating agent in an amount of from about 0% to about 1% by weight of the composition. In another embodiment, the coating comprises the coating agent in an amount of from about 2.5% to about 3.5% by weight of the composition. In still a further embodiment, the coating agent is OPADRY® CLEAR. In still a further embodiment, the coating agent is OPADRY® ORANGE.

In another embodiment, the total amount of dextromethorphan or a pharmaceutically acceptable salt thereof is 30 mg. In another embodiment, the total amount of dextromethorphan or a pharmaceutically acceptable salt thereof is 60 mg.

In one aspect, the invention includes an extended release pharmaceutical composition, wherein the pharmaceutical composition comprises:
  a) a sustained release formulation comprising:
    i. dextromethorphan HBr in an amount of from about 10% to about 40% by weight of the composition;
    ii. METHOCEL™ K4MCR in an amount of from about 5% to about 35% by weight of the composition;
    iii. METHOCEL™ K15MCR in an amount of from 0% to about 35% by weight of the composition;
    iv. lactose monohydrate in an amount of from about 10% to about 45% by weight of the composition.
    v. microcrystalline cellulose in an amount of from about 0% to about 40% by weight of the composition;
    vi. CAB-O-SIL® M-5 in an amount of from about 0% to about 1% by weight of the composition; and
    vii. magnesium stearate in an amount of from about 0% to about 2% by weight of the composition; and
  b) a coating.

In one embodiment, the coating comprising OPADRY® CLEAR in an amount of from about 0% to about 2% by weight of the composition. In a further embodiment, the pharmaceutical composition comprises OPADRY® CLEAR in an amount of from about 0% to about 1% by weight of the composition.

In one embodiment, the coating comprising OPADRY® ORANGE in an amount of from about 0% to about 5% by weight of the composition. In a further embodiment, the pharmaceutical composition comprises OPADRY® ORANGE in an amount of from about 0% to about 3% by weight of the composition. In another embodiment, the pharmaceutical composition comprises OPADRY® ORANGE in an amount of from about 2.5% to about 3.5% by weight of the composition. In a further embodiment, the pharmaceutical composition comprises OPADRY® ORANGE in an amount of about 3% by weight of the composition.

In one aspect, the invention includes a sustained release pharmaceutical tablet composition comprising: a) dextromethorphan or a pharmaceutically acceptable salt thereof in an amount of from about 5% to about 40% by weight of the composition; b) a controlled release agent in an amount of from about 5% to about 50% by weight of the composition; and c) a water soluble and/or insoluble diluent in an amount of from 0% to about 80% by weight of the composition;
  wherein the tablet has a volume of from about 0.0063 in$^3$ to about 0.0183 in$^3$, a surface area of from about 0.194 in$^2$ to about 0.395 in$^2$, and a surface area to volume ratio of from about 19.4 in$^{-1}$ to about 31.0 in$^{-1}$.

In one embodiment, the composition comprises dextromethorphan HBr.

In one embodiment, the composition comprises from about 15% to about 40% by weight of the composition of the controlled release agent.

In one embodiment, the controlled release agent is selected from one or more natural or partially or totally synthetic hydrophilic gums such as acacia, gum tragacanth, locust bean gum, guar gum, or karaya gum; cellulose ethers such as methylcellulose, hydroxomethylcellulose, hydroxypropyl methylcellulose (HPMC), hydroxypropyl cellulose, hydroxyethylcellulose, carboxymethylcellulose; proteinaceous substances such as agar, pectin, carrageen, and alginates; and other polymers such as carboxypolymethylene, gelatin, casein, zein, bentonite, magnesium aluminum silicate, polysaccharides, modified starch derivatives, ethyl cellulose, methacrylic acid-ethyl acrylate copolymers.

In another embodiment, the controlled release agent is a polymer or mixture of polymers.

In a further embodiment, the polymer or mixture of polymers comprises one or more cellulose ethers.

In a further embodiment, the controlled release agent comprises one or more types of hydroxypropyl methylcellulose, each independently having a viscosity ranging from 100 to about 50,000 mPa·s.

In still a further embodiment, the controlled release agent comprises a first hydroxypropyl methylcellulose, a second hydroxypropyl methylcellulose, or a combination thereof, wherein the first hydroxypropyl methylcellulose has
1) an apparent viscosity of from about 2,663 to about 4,970 mPa·s at 2 wt % in water;
2) a methyl substitution between about 22.0% and 24.0%; and
3) a hydroxypropyl substitution between about 7.5% and 9.5%; and the second hydroxypropyl methylcellulose has
1) an apparent viscosity of from about 13,275 to about 24,780 mPa·s at 2 wt % in water;
2) a methyl substitution between about 22.0% and 24.0%; and
3) a hydroxypropyl substitution between about 8.5% and 10.5%.

In one embodiment, the composition comprises from about 0% to about 35%, e.g. 5% to about 35% by weight of the composition of the first hydroxypropyl methylcellulose.

In another embodiment, the composition comprises from about 0% to about 30% by weight of the composition of the second hydroxypropyl methylcellulose.

In one embodiment, the composition comprises from about 0% to about 34%, e.g. 8% to about 34% by weight of the composition of the first hydroxypropyl methylcellulose.

In another embodiment, the composition comprises from about 0% to about 25% by weight of the composition of the second hydroxypropyl methylcellulose.

In a further embodiment, the weight percent of the first hydroxypropyl methylcellulose in the composition is selected from the group consisting of about 0%, 8.33%, 8.58%, 8.89%, 9.12%, 9.13%, 9.17%, 9.22%, 9.29%, 9.39%, 9.52%, 12.27%, 14.08%, 15.89%, 16.67%, 17.17%, 17.44%, 17.78%, 18.40%, 18.78%, 22.39%, 25.00%, 27.50%, 33.33%, and 33.91% and the weight percent of the second hydroxypropyl methylcellulose in the composition is selected from the group consisting of about 0%, 8.33%, 9.12%, 9.13%, 9.17%, 9.29%, 9.39%, 9.52%, 12.22%, 12.50%, 12.88%, 13.33%, 14.08%, 15.67%, 15.89%, 16.67%, 17.17%, 17.44%, 17.78%, 18.40%, 18.78%, and 23.01%.

In one embodiment, the composition comprises from about 10% to about 80% by weight of the composition of a water soluble and/or insoluble diluent. In one embodiment, the composition comprises from about 30% to about 60% by weight of the composition of a water soluble and/or insoluble diluent.

In one embodiment, the water soluble and/or insoluble diluent is selected from lactose, e.g. lactose monohydrate; celluloses, e.g. microcrystalline cellulose; calcium phosphates, e.g. dicalcium phosphate; starches; sugar alcohols, e.g. mannitol, sorbitol, and xylitol; sugars, e.g. sucrose; or any combination thereof.

In one embodiment, the diluent is selected from the group consisting of water soluble and water insoluble diluents, or a combination thereof.

In a further embodiment, the diluent is a combination of lactose monohydrate and microcrystalline cellulose.

In a further embodiment, the composition comprises from about 12% to about 34% by weight of the composition of lactose monohydrate and from about 13% to about 31% by weight of the composition of microcrystalline cellulose.

In another embodiment, the water soluble and/or insoluble diluent consists essentially of lactose monohydrate in an amount of from about 38% to about 42% by weight of the composition.

In still a further embodiment, the composition comprises about 14.89%, 17.24%, 17.30%, 17.82%, 18.45%, 19.49%, 19.60%, 22.25%, 22.64%, 23.25%, 23.55%, 23.75%, 23.76%, 24.00%, 24.67%, 25.02%, 25.41%, 25.87%, 26.23%, 26.32%, 27.73%, 27.80%, 29.73%, 29.74%, 29.86%, 29.99%, 30.28%, 30.60%, or 40.67% lactose monohydrate by weight of the composition and about 0%, 13.53%, 15.46%, 15.89%, 16.67%, 17.22%, 17.39%, 18.14%, 18.22%, 19.24%, 19.31%, 19.60%, 20.21%, 20.34%, 20.65%, 20.67%, 20.75%, 20.84%, 20.95%, 21.04%, 21.26%, 21.70%, 23.25%, 23.61%, 25.47%, 26.23%, 26.59%, or 30.37% microcrystalline cellulose by weight of the composition.

In one embodiment, the composition further comprises a glidant. In some embodiments, the glidant is selected from fumed silica, colloidal silica, precipitated silica, talc, or any combination thereof.

In one embodiment, the composition comprises a glidant in an amount of from about 0% to about 1% by weight of the composition.

In a further embodiment, the composition comprises a glidant in an amount of from about 0.3% to about 0.6% by weight of the composition.

In still a further embodiment, the composition comprises about 0.33%, 0.35%, 0.45%, 0.46%, 0.47%, 0.48%, 0.49%, or 0.50% glidant by weight of the composition.

In one embodiment, the glidant is fumed silica.

In a further embodiment, the fumed silica is commercially available as CAB-O-SIL® M-5.

In one embodiment, the composition further comprises a lubricant. In some embodiments, the lubricant is selected from magnesium stearate, stearic acid (stearin), hydrogenated castor oil, sodium stearyl fumarate, or any combination thereof.

In one embodiment, the composition comprises the lubricant in an amount of from about 0% to about 2% by weight of the composition.

In a further embodiment, the composition comprises the lubricant in an amount of from about 0.3% to about 1% by weight of the composition.

In still a further embodiment, the composition comprises about 0.35%, 0.49%, 0.50%, 0.67%, 0.69%, 0.70%, 0.71%, 0.72%, 0.73%, or 0.75% lubricant by weight of the composition.

In one embodiment, the lubricant is magnesium stearate.

In one embodiment, the composition further comprises an active coating.

In one embodiment, the active coating comprises:
a. dextromethorphan or a pharmaceutically acceptable salt thereof in an amount of from about 1% to about 10% by weight of the composition;
b. a film former in an amount of from about 0.1% to about 1.0% by weight of the composition;
c. a crystal growth inhibitor in an amount of from about 0.01% to about 3.0% by weight of the composition; and
d. a surfactant in an amount of from about 0.001% to about 0.5% by weight of the composition;
e. a plasticizer in an amount of from about 0% to about 0.5% by weight of the composition;

In one embodiment, the active coating comprises dextromethorphan HBr in an amount of about 1.0% to about 5.0% by weight of the composition.

In one embodiment, the film former in the active coating comprises a polyvinyl alcohol, a PVA/PEG graft copolymer, hydroxypropyl methylcellulose, copovidone, hydroxypropylcellulose, polyethylene glycol, or any combination thereof.

In another embodiment, the crystal growth inhibitor in the active coating comprises polyvinyl pyrrolidone, hypromellose, hydroxypropyl cellulose, hypromellose acetate succinate, or any combination thereof.

In another embodiment, the surfactant in the active coating comprises docusate sodium, sodium lauryl sulfate, sorbitan esters, glyceryl monooleate, lauric acid, polysorbate 80, polyoxyethylene derivatives, vitamin E polyethylene glycol succinate, or any combination thereof.

In another embodiment, the plasticizer in the active coating comprises acetyltributyl citrate, triethyl citrate, polyethylene glycol, triacetin, dibutyl phthalate, propylene glycol, sorbitol, or any combination thereof.

In a further embodiment, the film former is hydroxypropyl methylcellulose.

In another further embodiment, the crystal growth inhibitor is polyvinyl pyrrolidone.

In another further embodiment, the surfactant is sodium lauryl sulfate.

In another further embodiment, the plasticizer is polyethylene glycol.

In still a further embodiment, the film former is hydroxypropyl methylcellulose having an apparent viscosity range of about 2.4-7 mPa·s at 2 wt % in water, a methyl substitution range of about 28.0%-30.0%, and a hydroxypropyl substitution range of about 7.0%-12.0%.

In another further embodiment, the crystal growth inhibitor is povidone K28-K32 (as used herein, "povidone K28-K32" is synonymous with "povidone K30") or the crystal growth inhibitor is povidone K12.

In one embodiment, the polyvinylpyrrolidone is povidone K28-K32.

In another further embodiment, the plasticizer is polyethylene glycol 400 or polyethylene glycol 8000.

In one embodiment, the active coating further comprises a polyvinyl alcohol—polyethylene glycol copolymer.

In a further embodiment, the polyvinyl alcohol—polyethylene glycol copolymer has an average molecular weight of about 45,000 daltons, and comprises about 75% polyvinyl alcohol units and about 25% polyethylene glycol units by weight.

In one embodiment, the active coating further comprises a flavoring agent, cooling agent, sweetener, or salivation agent.

In another embodiment, the composition further comprises a film coating.

In one embodiment, the film coating is present in an amount from about 0.1% to about 5% by weight of the composition.

In a further embodiment, the film coating is present in an amount from about 0.45% to about 0.55% by weight of the composition.

In another further embodiment, the film coating is present in an amount from about 2.5% to about 3.5% by weight of the composition.

In one embodiment, the film coating comprises hypromellose, polyethylene glycol, and optionally, polydextrose, talc, a pigment, and Titanium dioxide.

In another embodiment, the film coating composition further comprises a flavoring agent, cooling agent, sweetener, or salivation agent.

In a further embodiment, the film coating is commercially available as OPADRY®.

In one embodiment, the total amount of dextromethorphan or a pharmaceutically acceptable salt thereof in the composition is about 60 mg.

In another embodiment, the total amount of dextromethorphan or a pharmaceutically acceptable salt thereof in the composition is about 30 mg.

In one aspect, the invention includes a sustained release pharmaceutical tablet composition comprising:
a) a core tablet sustained release formulation comprising:
  i. dextromethorphan HBr in an amount of from about 5.0% to about 40.0% by weight of the composition;
  ii. hydroxypropyl methylcellulose having an apparent viscosity of from about 2,663 to about 4,970 mPa·s at 2 wt % in water, a methyl substitution between about 22.0% and 24.0%, and a hydroxypropyl substitution between about 7.5% and 9.5%, in an amount of from about 0% to about 45.0%, e.g. 5.0% to about 45.0% by weight of the composition;
  iii. hydroxypropyl methylcellulose having an apparent viscosity of from about 13,275 to about 24,780 mPa·s, a methyl substitution between about 22.0% and 24.0%, and a hydroxypropyl substitution between about 8.5% and 10.5%, in an amount of from 0% to about 30.0% by weight of the composition;
  iv. lactose monohydrate in an amount of from about 10.0% to about 50.0% by weight of the composition.
  v. microcrystalline cellulose in an amount of from 0% to about 35.0% by weight of the composition;
  vi. fumed silica in an amount of from 0% to about 1.0% by weight of the composition; and
  vii. magnesium stearate in an amount of from about 0.20% to about 1.0% by weight of the composition; and
b) optionally, an active coating comprising
  i. dextromethorphan or a pharmaceutically acceptable salt thereof in an amount of from about 1.0% to about 10.0% by weight of the composition;
  ii. hydroxypropyl methylcellulose having an apparent viscosity range of about 2.4-7 mPa·s at 2 wt % in water, a methyl substitution range of about 28.0%-30.0%, and a hydroxypropyl substitution range of about 7.0%-12.0% in an amount of from 0% to about 3.0% by weight of the composition;
  iii. polyvinyl pyrrolidone in an amount of from 0% to about 5.0% by weight of the composition;
  iv. sodium lauryl sulfate in an amount of from 0% to about 0.50% by weight of the composition;

v. PEG 400 or PEG 8000 in an amount of from 0% to about 3.0% by weight of the composition;

c) optionally, a film coating.

In one aspect, the invention includes a sustained release pharmaceutical tablet composition comprising:
   a) a core tablet sustained release formulation comprising:
      i. dextromethorphan HBr in an amount of from about 5.0% to about 40.0% by weight of the composition;
      ii. one, or a mixture of two or more controlled release hydroxypropyl methylcellulose polymers, wherein the polymer or mixture of polymers has an apparent viscosity of from about 2,663 to about 4,970 mPa·s at 2 wt % in water, a methyl substitution between about 22.0% and 24.0%, and a hydroxypropyl substitution between about 7.5% and 9.5%, in an amount of from about 0% to about 45.0%, e.g. 5.0% to about 45.0% by weight of the composition;
      iii. hydroxypropyl methylcellulose having an apparent viscosity of from about 13,275 to about 24,780 mPa·s, a methyl substitution between about 22.0% and 24.0%, and a hydroxypropyl substitution between about 8.5% and 10.5%, in an amount of from 0% to about 30.0% by weight of the composition;
      iv. one or more soluble and/or insoluble diluents selected from lactose monohydrate in an amount of from about 10.0% to about 50.0% by weight of the composition, and microcrystalline cellulose in an amount of from 0% to about 35.0% by weight of the composition;
   b) optionally,
      i. a glidant, comprising fumed silica in an amount of from 0% to about 1.0% by weight of the composition, and
      ii. a lubricant, comprising magnesium stearate in an amount of from about 0.20% to about 1.0% by weight of the composition;
   c) optionally, an active coating comprising:
      i. dextromethorphan or a pharmaceutically acceptable salt thereof in an amount of from about 1.0% to about 10.0% by weight of the composition;
      ii. hydroxypropyl methylcellulose having an apparent viscosity range of about 2.4-7 mPa·s at 2 wt % in water, a methyl substitution range of about 28.0%-30.0%, and a hydroxypropyl substitution range of about 7.0%-12.0% in an amount of from 0% to about 3.0% by weight of the composition;
      iii. polyvinyl pyrrolidone in an amount of from 0% to about 5.0% by weight of the composition;
      iv. sodium lauryl sulfate in an amount of from 0% to about 0.50% by weight of the composition;
      v. PEG 400 or PEG 8000 in an amount of from 0% to about 3.0% by weight of the composition; and
   d) optionally, a film coating.

In one aspect, the invention includes a sustained release pharmaceutical tablet composition comprising:
   a) a core tablet sustained release formulation comprising:
      i. dextromethorphan HBr in an amount of from about 5.0% to about 40.0% by weight of the composition;
      ii. controlled release polymers, preferably hydroxypropyl methylcellulose of different viscosities alone or in combination, wherein the total polymer has an apparent viscosity of from about 2,663 to about 4,970 mPa·s at 2 wt % in water, a methyl substitution between about 22.0% and 24.0%, and a hydroxypropyl substitution between about 7.5% and 9.5%, in an amount of from about 0% to about 45.0%, e.g. 5.0% to about 45.0% by weight of the composition; hydroxypropyl methylcellulose having an apparent viscosity of from about 13,275 to about 24,780 mPa·s, a methyl substitution between about 22.0% and 24.0%, and a hydroxypropyl substitution between about 8.5% and 10.5%, in an amount of from 0% to about 30.0% by weight of the composition;
      iii. water soluble and/or insoluble diluents preferably lactose monohydrate in an amount of from about 10.0% to about 50.0% by weight of the composition and microcrystalline cellulose in an amount of from 0% to about 35.0% by weight of the composition;
   b) optionally, a glidant, preferably fumed silica in an amount of from 0% to about 1.0% by weight of the composition; and a lubricant, preferably magnesium stearate in an amount of from about 0.20% to about 1.0% by weight of the composition; and
   c) optionally, an active coating comprising:
      i. dextromethorphan or a pharmaceutically acceptable salt thereof in an amount of from about 1.0% to about 10.0% by weight of the composition;
      ii. hydroxypropyl methylcellulose having an apparent viscosity range of about 2.4-7 mPa·s at 2 wt % in water, a methyl substitution range of about 28.0%-30.0%, and a hydroxypropyl substitution range of about 7.0%-12.0% in an amount of from 0% to about 3.0% by weight of the composition;
      iii. polyvinyl pyrrolidone in an amount of from 0% to about 5.0% by weight of the composition;
      iv. sodium lauryl sulfate in an amount of from 0% to about 0.50% by weight of the composition;
      v. PEG 400 or PEG 8000 in an amount of from 0% to about 3.0% by weight of the composition;
   d) optionally, a film coating.

In another aspect, the invention includes a sustained release pharmaceutical tablet composition comprising:
   a) a core tablet sustained release formulation comprising:
      i. dextromethorphan or a pharmaceutically acceptable salt thereof in an amount of from about 5% to about 40% by weight of the composition;
      ii. a controlled release agent in an amount of from about 5% to about 50% by weight of the composition; and
      iii. a water soluble and/or insoluble diluent in an amount of from 0% to about 80% by weight of the composition;
   b) optionally,
      i. a glidant, comprising fumed silica in an amount of from 0% to about 1.0% by weight of the composition, and
      ii. a lubricant, comprising magnesium stearate in an amount of from about 0.20% to about 1.0% by weight of the composition;
   c) an active coating comprising:
      i. dextromethorphan or a pharmaceutically acceptable salt thereof in an amount of from about 1.0% to about 10.0% by weight of the composition;
      ii. a film former in an amount of from 0% to about 5.0% by weight of the composition;
      iii. polyvinyl pyrrolidone in an amount of from 0% to about 5.0% by weight of the composition;
      iv. optionally, sodium lauryl sulfate in an amount of from 0% to about 0.50% by weight of the composition;
      v. optionally, PEG 400 or PEG 8000 in an amount of from 0% to about 3.0% by weight of the composition; and
   d) optionally, a film coating.

In one embodiment of this aspect,
a) the core tablet sustained release formulation comprises
 i. dextromethorphan HBr in an amount of from about 12.5% to about 30.0% by weight of the composition;
 ii. hydroxypropyl methylcellulose having an apparent viscosity of from about 2,663 to about 4,970 mPa·s at 2 wt % in water, a methyl substitution between about 22.0% and 24.0%, and a hydroxypropyl substitution between about 7.5% and 9.5%, in an amount of from about 0% to about 34.0%, e.g. about 8.0% to about 34.0% by weight of the composition;
 iii. hydroxypropyl methylcellulose having an apparent viscosity of from about 13,275 to about 24,780 mPa·s, a methyl substitution between about 22.0% and 24.0%, and a hydroxypropyl substitution between about 8.5% and 10.5%, in an amount of from 0% to about 25.0% by weight of the composition;
 iv. lactose monohydrate in an amount of from about 14.0% to about 41.0% by weight of the composition.
 v. microcrystalline cellulose in an amount of from 0% to about 31.0% by weight of the composition;
 vi. fumed silica in an amount of from about 0.30% to about 0.52% by weight of the composition; and
 vii. magnesium stearate in an amount of from about 0.33% to about 0.77% by weight of the composition; and
b) the active coating is absent or comprises
 i. dextromethorphan or a pharmaceutically acceptable salt thereof in an amount of from about 1.0% to about 5.0% by weight of the composition;
 ii. hydroxypropyl methylcellulose having an apparent viscosity range of about 2.4-7 mPa·s at 2 wt % in water, a methyl substitution range of about 28.0%-30.0%, and a hydroxypropyl substitution range of about 7.0%-12.0% in an amount of from 0% to about 1.0% by weight of the composition;
 iii. polyvinyl pyrrolidone in an amount of from 0% to about 1.5% by weight of the composition;
 iv. sodium lauryl sulfate in an amount of from 0% to about 0.10% by weight of the composition;
 v. PEG 400 or PEG 8000 in an amount of from 0% to about 1.0% by weight of the composition;
c) the film coating is absent or comprises a polymer and a plasticizer.
In another embodiment of this aspect,
a) the core tablet sustained release formulation comprises
 i. dextromethorphan HBr in an amount selected from about 12.50%, 17.44%, 18.40%, 23.26%, 23.28%, 23.37%, 23.50%, 23.83%, 25.00%, 25.75%, 26.02%, 26.67%, and 28.17% by weight of the composition;
 ii. hydroxypropyl methylcellulose having an apparent viscosity of from about 2,663 to about 4,970 mPa·s at 2 wt % in water, a methyl substitution between about 22.0% and 24.0%, and a hydroxypropyl substitution between about 7.5% and 9.5%, in an amount selected from the group consisting of about 0%, 8.33%, 8.58%, 8.89%, 9.12%, 9.13%, 9.17%, 9.22%, 9.29%, 9.39%, 9.52%, 12.27%, 14.08%, 15.89%, 16.67%, 17.17%, 17.44%, 17.78%, 18.40%, 18.78%, 22.39%, 25.00%, 27.50%, 33.33%, and 33.91% by weight of the composition;
 iii. hydroxypropyl methylcellulose having an apparent viscosity of from about 13,275 to about 24,780 mPa·s, a methyl substitution between about 22.0% and 24.0%, and a hydroxypropyl substitution between about 8.5% and 10.5%, in an amount selected from the group consisting of about 0%, 8.33%, 9.12%, 9.13%, 9.17%, 9.29%, 9.39%, 9.52%, 12.22%, 12.50%, 12.88%, 13.33%, 14.08%, 15.67%, 15.89%, 16.67%, 17.17%, 17.44%, 17.78%, 18.40%, 18.78%, and 23.01% by weight of the composition;
 iv. lactose monohydrate in an amount selected from about 14.89%, 17.24%, 17.30%, 17.82%, 18.45%, 19.49%, 19.60%, 22.25%, 22.64%, 23.25%, 23.55%, 23.75%, 23.76%, 24.00%, 24.67%, 25.02%, 25.41%, 25.87%, 26.23%, 26.32%, 27.73%, 27.80%, 29.73%, 29.74%, 29.86%, 29.99%, 30.28%, 30.60%, and 40.67% by weight of the composition.
 v. microcrystalline cellulose in an amount selected from about 0%, 13.53%, 15.46%, 15.89%, 16.67%, 17.22%, 17.39%, 18.14%, 18.22%, 19.24%, 19.31%, 19.60%, 20.21%, 20.34%, 20.65%, 20.67%, 20.75%, 20.84%, 20.95%, 21.04%, 21.26%, 21.70%, 23.25%, 23.61%, 25.47%, 26.23%, 26.59%, and 30.37% by weight of the composition;
 vi. fumed silica in an amount selected from about 0.33%, 0.35%, 0.45%, 0.46%, 0.47%, 0.48%, 0.49%, or 0.50% by weight of the composition; and
 vii. magnesium stearate in an amount selected from about 0.35%, 0.49%, 0.50%, 0.67%, 0.69%, 0.70%, 0.71%, 0.72%, 0.73%, and 0.75% by weight of the composition;
b) the active coating is absent or comprises
 i. dextromethorphan or a pharmaceutically acceptable salt thereof in an amount selected from about 1.86%, 4.11%, 4.12%, 4.15%, and 4.21% by weight of the composition;
 ii. hydroxypropyl methylcellulose having an apparent viscosity range of about 2.4-7 mPa·s at 2 wt % in water, a methyl substitution range of about 28.0%-30.0%, and a hydroxypropyl substitution range of about 7.0%-12.0% in an amount selected from about 0%, 0.41%, 0.47%, and 0.91% by weight of the composition;
 iii. polyvinyl pyrrolidone in an amount selected from about 0%, 0.41%, 0.91%, 1.37%, and 1.38% by weight of the composition;
 iv. sodium lauryl sulfate in an amount selected from about 0%, 0.004%, 0.01%, and 0.06% by weight of the composition;
 v. PEG 400 or PEG 8000 in an amount selected from about 0%, 0.20%, and 0.46% by weight of the composition; and
c) the film coating is absent or comprises a polymer and a plasticizer.
In one embodiment,
a) the core tablet sustained release formulation comprises
 i. dextromethorphan HBr in an amount of from about 12.5% to about 30.0% by weight of the composition;
 ii. hydroxypropyl methylcellulose having an apparent viscosity of from about 2,663 to about 4,970 mPa·s at 2 wt % in water, a methyl substitution between about 22.0% and 24.0%, and a hydroxypropyl substitution between about 7.5% and 9.5%, in an amount of from about 0% to about 34.0%, e.g. 8.0% to about 34.0% by weight of the composition;
 iii. hydroxypropyl methylcellulose having an apparent viscosity of from about 13,275 to about 24,780 mPa·s, a methyl substitution between about 22.0% and 24.0%, and a hydroxypropyl substitution between about 8.5% and 10.5%, in an amount of from 0% to about 25.0% by weight of the composition;
iv. lactose monohydrate in an amount of from about 14.0% to about 41.0% by weight of the composition.
v. microcrystalline cellulose in an amount of from 0% to about 31.0% by weight of the composition;
vi. fumed silica in an amount of from about 0.30% to about 0.52% by weight of the composition; and
vii. magnesium stearate in an amount of from about 0.33% to about 0.77% by weight of the composition; and b) the active coating is absent or comprises
i. dextromethorphan or a pharmaceutically acceptable salt thereof in an amount of from about 1.0% to about 5.0% by weight of the composition;
ii. hydroxypropyl methylcellulose having an apparent viscosity range of about 2.4-7 mPa·s at 2 wt % in water, a methyl substitution range of about 28.0%-30.0%, and a hydroxypropyl substitution range of about 7.0%-12.0% in an amount of from 0% to about 1.0% by weight of the composition;
iii. polyvinyl pyrrolidone in an amount of from 0% to about 1.5% by weight of the composition;
iv. sodium lauryl sulfate in an amount of from 0% to about 0.10% by weight of the composition;
v. PEG 400 or PEG 8000 in an amount of from 0% to about 1.0% by weight of the composition;

c) the film coating is absent or comprises a polymer and a plasticizer.

In a further embodiment,
a) the core tablet sustained release formulation comprises
i. dextromethorphan HBr in an amount selected from about 12.50%, 17.44%, 18.40%, 23.26%, 23.28%, 23.37%, 23.50%, 23.83%, 25.00%, 25.75%, 26.02%, 26.67%, and 28.17% by weight of the composition;
ii. hydroxypropyl methylcellulose having an apparent viscosity of from about 2,663 to about 4,970 mPa·s at 2 wt % in water, a methyl substitution between about 22.0% and 24.0%, and a hydroxypropyl substitution between about 7.5% and 9.5%, in an amount selected from the group consisting of about 0%, 8.33%, 8.58%, 8.89%, 9.12%, 9.13%, 9.17%, 9.22%, 9.29%, 9.39%, 9.52%, 12.27%, 14.08%, 15.89%, 16.67%, 17.17%, 17.44%, 17.78%, 18.40%, 18.78%, 22.39%, 25.00%, 27.50%, 33.33%, and 33.91% by weight of the composition;
iii. hydroxypropyl methylcellulose having an apparent viscosity of from about 13,275 to about 24,780 mPa·s, a methyl substitution between about 22.0% and 24.0%, and a hydroxypropyl substitution between about 8.5% and 10.5%, in an amount selected from about 0%, 8.33%, 9.12%, 9.13%, 9.17%, 9.29%, 9.39%, 9.52%, 12.22%, 12.50%, 12.88%, 13.33%, 14.08%, 15.67%, 15.89%, 16.67%, 17.17%, 17.44%, 17.78%, 18.40%, 18.78%, and 23.01% by weight of the composition;
iv. lactose monohydrate in an amount selected from about 14.89%, 17.24%, 17.30%, 17.82%, 18.45%, 19.49%, 19.60%, 22.25%, 22.64%, 23.25%, 23.55%, 23.75%, 23.76%, 24.00%, 24.67%, 25.02%, 25.41%, 25.87%, 26.23%, 26.32%, 27.73%, 27.80%, 29.73%, 29.74%, 29.86%, 29.99%, 30.28%, 30.60%, and 40.67% by weight of the composition;
v. microcrystalline cellulose in an amount selected from about 0%, 13.53%, 15.46%, 15.89%, 16.67%, 17.22%, 17.39%, 18.14%, 18.22%, 19.24%, 19.31%, 19.60%, 20.21%, 20.34%, 20.65%, 20.67%, 20.75%, 20.84%, 20.95%, 21.04%, 21.26%, 21.70%, 23.25%, 23.61%, 25.47%, 26.23%, 26.59%, and 30.37% by weight of the composition;
vi. fumed silica in an amount selected from about 0.33%, 0.35%, 0.45%, 0.46%, 0.47%, 0.48%, 0.49%, or 0.50% by weight of the composition; and
vii. magnesium stearate in an amount selected from about 0.35%, 0.49%, 0.50%, 0.67%, 0.69%, 0.70%, 0.71%, 0.72%, 0.73%, and 0.75% by weight of the composition;

b) the active coating is absent or comprises
i. dextromethorphan or a pharmaceutically acceptable salt thereof in an amount selected from about 1.86%, 4.11%, 4.12%, 4.15%, and 4.21% by weight of the composition;
ii. hydroxypropyl methylcellulose having an apparent viscosity range of about 2.4-7 mPa·s at 2 wt % in water, a methyl substitution range of about 28.0%-30.0%, and a hydroxypropyl substitution range of about 7.0%-12.0% in an amount selected from about 0%, 0.41%, 0.47%, and 0.91% by weight of the composition;
iii. polyvinyl pyrrolidone in an amount selected from about 0%, 0.41%, 0.91%, 1.37%, and 1.38% by weight of the composition;
iv. sodium lauryl sulfate in an amount selected from about 0%, 0.004%, 0.01%, and 0.06% by weight of the composition;
v. PEG 400 or PEG 8000 in an amount selected from about 0%, 0.20%, and 0.46% by weight of the composition; and c) the film coating is absent or comprises a polymer and a plasticizer.

In one embodiment,
a) the core tablet sustained release formulation comprises
i. about 23.28% of dextromethorphan HBr by weight of the composition;
ii. about 9.13% of hydroxypropyl methylcellulose having an apparent viscosity of from about 2,663 to about 4,970 mPa·s at 2 wt % in water, a methyl substitution between about 22.0% and 24.0%, and a hydroxypropyl substitution between about 7.5% and 9.5%, by weight of the composition;
iii. about 9.13% of hydroxypropyl methylcellulose having an apparent viscosity of from about 13,275 to about 24,780 mPa·s, a methyl substitution between about 22.0% and 24.0%, and a hydroxypropyl substitution between about 8.5% and 10.5%, by weight of the composition;
iv. about 29.74% of lactose monohydrate by weight of the composition;
v. about 20.67% microcrystalline cellulose by weight of the composition;
vi. about 0.47% fumed silica by weight of the composition; and
vii. about 0.70% magnesium stearate by weight of the composition;

b) the active coating comprises
i. about 4.11% dextromethorphan HBr by weight of the composition;
ii. about 0.91% polyvinylpyrrolidone by weight of the composition;
iii. about 0.91% of hydroxypropyl methylcellulose having an apparent viscosity range of 2.4-3.6 mPa·s, a methyl substitution of 28.0%-30.0% (inclusive), and a hydroxypropyl substitution of 7.0%-12.0% (inclusive) by weight of the composition;
iv. about 0.46% of polyethylene glycol by weight of the composition; and
iv. about 0.01% of sodium lauryl sulfate by weight of the composition; and
c) the film coating comprises a polymer, plasticizer and pigment.

In a further embodiment, the film coating comprises hypromellose, polyethylene glycol, and optionally, one or more of polydextrose, talc, a pigment, and titanium dioxide.

In still a further embodiment, the pharmaceutical composition comprises the film coating in an amount of about 0.50% by weight of the composition.

In one embodiment,
a) the core tablet sustained release formulation comprises
   i. about 25.00% of dextromethorphan HBr by weight of the composition;
   ii. about 8.33% of hydroxypropyl methylcellulose having an apparent viscosity of from about 2,663 to about 4,970 mPa·s at 2 wt % in water, a methyl substitution between about 22.0% and 24.0%, and a hydroxypropyl substitution between about 7.5% and 9.5%, by weight of the composition;
   iii. about 12.50% of hydroxypropyl methylcellulose having an apparent viscosity of from about 13,275 to about 24,780 mPa·s, a methyl substitution between about 22.0% and 24.0%, and a hydroxypropyl substitution between about 8.5% and 10.5%, by weight of the composition;
   iv. about 24.67% of lactose monohydrate by weight of the composition;
   v. about 25.47% microcrystalline cellulose by weight of the composition;
   vi. about 0.45% fumed silica by weight of the composition; and
   vii. about 0.67% magnesium stearate by weight of the composition;
b) the active coating is absent; and
c) the film coating comprises a polymer, plasticizer and pigment.

In another embodiment,
a) the core tablet sustained release formulation comprises
   i. about 25.00% of dextromethorphan HBr by weight of the composition;
   ii. about 16.67% of hydroxypropyl methylcellulose having an apparent viscosity of from about 2,663 to about 4,970 mPa·s at 2 wt % in water, a methyl substitution between about 22.0% and 24.0%, and a hydroxypropyl substitution between about 7.5% and 9.5%, by weight of the composition;
   iii. about 16.67% of hydroxypropyl methylcellulose having an apparent viscosity of from about 13,275 to about 24,780 mPa·s, a methyl substitution between about 22.0% and 24.0%, and a hydroxypropyl substitution between about 8.5% and 10.5%, by weight of the composition;
   iv. about 17.30% of lactose monohydrate by weight of the composition;
   v. about 20.34% microcrystalline cellulose by weight of the composition;
   vi. about 0.45% fumed silica by weight of the composition; and
   vii. about 0.67% magnesium stearate by weight of the composition;
b) the active coating is absent; and
c) the film coating comprises a polymer, plasticizer and pigment.

In a further embodiment, the film coating comprises hypromellose, polyethylene glycol, and optionally, one or more of polydextrose, talc, a pigment, and titanium dioxide.

In still a further embodiment, the pharmaceutical composition comprises the film coating in an amount of about 2.91% by weight of the composition.

In another further embodiment, the total weight of the tablet is about 240 mg.

In another embodiment, the active coating further comprises a polyvinyl alcohol—polyethylene glycol copolymer.

In a further embodiment, the polyvinyl alcohol—polyethylene glycol copolymer has an average molecular weight of about 45,000 daltons, and comprises about 75% polyvinyl alcohol units and about 25% polyethylene glycol units by weight.

In one embodiment, the active coating further comprises a flavoring agent, cooling agent, sweetener, or salivation agent.

In another embodiment, the film coating further comprises a flavoring agent, cooling agent, sweetener, or salivation agent.

In one embodiment, the tablet has a mass of from about 200 mg to about 326 mg, a volume of from about 0.0106 in$^3$ to about 0.0183 in$^3$, a surface area of from about 0.252 in$^2$ to about 0.395 in$^2$, and a surface area to volume ratio of from about 19.4 in$^{-1}$ to about 23.9 in$^{-1}$.

In a further embodiment, the tablet has a mass selected from about 213 mg, about 214 mg, about 215 mg, about 217 mg, about 218 mg, about 219 mg, about 225 mg, about 233 mg, about 240 mg, and about 326 mg.

In one embodiment, the tablet has a mass of from about 110 mg to about 172 mg, a volume of from about 0.0063 in$^3$ to about 0.0088 in$^3$, a surface area of from about 0.194 in$^2$ to about 0.229 in$^2$, and a surface area to volume ratio of from about 26.2 in$^{-1}$ to about 31.0 in$^{-1}$.

In a further embodiment, the tablet has a mass selected from about 120 mg, about 172 mg and about 240 mg.

In one embodiment, the total amount of dextromethorphan or a pharmaceutically acceptable salt thereof is about 60 mg.

In another embodiment, the total amount of dextromethorphan or a pharmaceutically acceptable salt thereof is about 30 mg.

In one embodiment, the hydroxypropyl methylcellulose having an apparent viscosity of from about 2,663 to about 4,970 mPa·s, a methyl substitution between about 22.0% and 24.0%, and a hydroxypropyl substitution between about 7.5% and 9.5% is sold under the trademark METHOCEL™ K4M Premium CR.

In one embodiment, the hydroxypropyl methylcellulose having an apparent viscosity of from about 13,275 to about 24,780 mPa·s, a methyl substitution between about 22.0% and 24.0%, and a hydroxypropyl substitution between about 8.5% and 10.5% is sold under the trademark METHOCEL™ K15M Premium CR.

In one embodiment, the hydroxypropyl methylcellulose having an apparent viscosity range of 2.4-3.6 mPa·s, a methyl substitution of 28.0%-30.0% (inclusive), and a hydroxypropyl substitution of 7.0%-12.0% (inclusive) is sold under the trademark METHOCEL™ E3 LV.

In one embodiment, less than 40% of the dextromethorphan or a pharmaceutically acceptable salt thereof is released from the tablet in 30 minutes, when the tablet is stirred at 75 rpm in 900 mL of 0.1 N HCl at 37° C.±0.5° C.

In another embodiment, the dextromethorphan or a pharmaceutically acceptable salt thereof is released from the tablet in 1 hour, when the tablet is stirred at 75 rpm in 900 mL of 0.1 N HCl at 37° C.±0.5° C.

In another embodiment, the dextromethorphan or a pharmaceutically acceptable salt thereof is released from the tablet in 2 hour, when the tablet is stirred at 75 rpm in 900 mL of 0.1 N HCl at 37° C.±0.5° C.

In another embodiment, the dextromethorphan or a pharmaceutically acceptable salt thereof is released from the tablet in 4 hours, when the tablet is stirred at 75 rpm in 900 mL of 0.1 N HCl at 37° C.±0.5° C.

In another embodiment, more than 70% of the dextromethorphan or a pharmaceutically acceptable salt thereof is released from the tablet in 8 hours, when the tablet is stirred at 75 rpm in 900 mL of 0.1 N HCl at 37° C.±0.5° C.

In one aspect, the invention includes a method of treating cough in a patient in need thereof, comprising administering to a patient in need thereof a pharmaceutical composition described herein.

EXAMPLES

Example 1: Preparation of a 60 mg Dextromethorphan HBr Extended Release Tablet with an Active Coating (and in Some Cases a Film Coating) (Tablet 1)

Core Tablet:

Dextromethorphan HBr 3.50 kg, METHOCEL™ K4MCR 1.37 kg, METHOCEL™ K15MCR 1.37 kg, CAB-O-SIL® M-5 0.070 kg (70 g), lactose monohydrate 4.47 kg, and microcrystalline cellulose (MCC) 3.11 kg are added to a vibratory sifter (ASTM #20) and sifted into a 2.0 ft³, V-shell blender. The resulting sifted mixture is then blended for 10 minutes at 250 RPM. Magnesium stearate 0.105 kg (105 g) is then added to a sieve (ASTM #20) and added to the mixture contained in the blender. The resulting mixture is then blended for 4 minutes at 100 RPM. The mixture is then transferred to a Manesty Unipress with B-tooling (0.3380" diameter, round, plain-faced) and pressed into tablets to target hardness of 7.0 SCU.

Active Coating:

Purified water at 50-70° C. 13.0 kg is mixed with hypromellose (METHOCEL™ E3 LV (METHOCEL™ E3 Prem or Kollicoat IR (PVA/PEG copolymer) can also be used) 0.205 kg (205 g) and PEG 400 (also called polyethylene glycol 400) 0.103 kg (103 g) to form pre-mix solution #1. In a separate container, purified water at 50-70° C. 14.4 kg is mixed with dextromethorphan HBr 0.924 kg (924 g) and povidone K30 0.205 kg (205 g) to form pre-mix solution #2. Pre-mix solutions 1 and 2 are then mixed together for no less than 15 minutes while maintaining a solution temperature of 50-70° C. and sodium lauryl sulfate is then added 2.05 g (2,050 mg) and mixed to form an active coating solution. The resulting coating solution is sprayed onto the core tablets in a Compulab 24" Pan with 60100 nozzles, 134255-45 aircaps, 2 spray system 7310-1/4 Jauco SS, 7-8 o'clock gun position, and 5-7 inch nozzle distance for tablet bed. Target outlet temperature of 44° C. (range: 30-50° C.), air flow of 350 cfm (range: 300-400 cfm), atomization air pressure of 40 psi (range: 30-60 psi), pan speed of 15 rpm (range: 12-18 rpm), and spray rate of 40 g/min (range: 20-60 g/min).

Film Coating:

Purified water 2.38 kg is mixed with OPADRY® Clear 0.125 kg to form a solution, which is then sprayed onto the coated tablets described above in a second Compulab 24" Pan with 60100 nozzles, 134255-45 aircaps, 2 spray system 7310-1/4 Jauco SS, 7-8 o'clock gun position, and 5-7 inch nozzle distance for tablet bed. Target outlet temperature of 44° C. (range: 30-55° C.), air flow of 350 cfm (range: 300-400 cfm), atomization air pressure of 40 psi (range: 30-60 psi), pan speed of 15 rpm (range: 12-18 rpm), and spray rate of 40 g/min (range: 20-60 g/min).

TABLE 1a 60 mg Dextromethorphan HBr Tablet formulation 1

| | Material Name | Tablet 1 mg/tab (% w/w) |
|---|---|---|
| Core Tablet | Dextromethorphan HBr | 51.00 (23.28) |
| | Methocel ™ K4M Premium CR | 20.00 (9.13) |
| | Methocel ™ K15M Premium CR | 20.00 (9.13) |
| | Lactose Monohydrate Fast-Flo | 65.17 (29.74) |
| | MCC PH-102 | 45.28 (20.67) |
| | Cabosil ® M-5 | 1.02 (0.47) |
| | Magnesium Stearate | 1.53 (0.70) |
| | Total Core Tablet Wt. (mg) | 204.00 |
| Active Coating | Dextromethorphan HBr | 9.00 (4.11) |
| | Povidone K30 | 2.00 (0.91) |
| | Methocel ™ E3 LV | 2.00 (0.91) |
| | Polyethylene Glycol 400 | 1.00 (0.46) |
| | Sodium Lauryl Sulfate | 0.02 (0.01) |
| Film Coating | Opadry ® Clear | 1.09 (0.50) |
| Total Coated Tablet Wt. (mg) | | 219.11 |

TABLE 1b 60 mg Dextromethorphan HBr Tablet formulations 2-5

| Material Name | Tablet 2 mg/tab (% w/w) | Tablet 3 mg/tab (% w/w) | Tablet 4 mg/tab (% w/w) | Tablet 5 mg/tab (% w/w) |
|---|---|---|---|---|
| Core Tablet | | | | |
| Dextromethorphan HBr | 51.00 (23.83) | 51.00 (23.50) | 51.00 (23.37) | 51.00 (23.26) |
| Methocel ™ K4M Premium CR | 34.00 (15.89) | 20.00 (9.22) | 20.00 (9.17) | 20.00 (9.12) |
| Methocel ™ K15M Premium CR | 34.00 (15.89) | 34.00 (15.67) | 20.00 (9.17) | 20.00 (9.12) |
| Lactose Monohydrate Fast-Flo | 48.45 (22.64) | 56.91 (26.23) | 65.17 (29.86) | 65.17 (29.73) |
| MCC PH-102 | 34.00 (15.89) | 39.54 (18.22) | 45.28 (20.75) | 45.28 (20.65) |
| Cabosil ® M-5 | 1.02 (0.48) | 1.02 (0.47) | 1.02 (0.47) | 1.02 (0.47) |
| Magnesium Stearate | 1.53 (0.71) | 1.53 (0.71) | 1.53 (0.70) | 1.53 (0.70) |
| Total Core Tablet Wt. (mg) | 204.00 | 204.00 | 204.00 | 204.00 |

TABLE 1b-continued 60 mg Dextromethorphan HBr Tablet formulations 2-5

| Material Name | Tablet 2 mg/tab (% w/w) | Tablet 3 mg/tab (% w/w) | Tablet 4 mg/tab (% w/w) | Tablet 5 mg/tab (% w/w) |
|---|---|---|---|---|
| Active Coating | | | | |
| Dextromethorphan HBr | 9.00 (4.21) | 9.00 (4.15) | 9.00 (4.12) | 9.00 (4.11) |
| Methocel ™ E3 Prem | 1.00 (0.47) | 0 | 0 | 0 |
| N-C Cooling Mint Flavor | 0.01 (0.005) | 0 | 0 | 0 |
| Kollicoat IR (PVA/PEG copolymer) | 0 | 0 | 0 | 2.00 (0.91) |
| Povidone K30 | 0 | 3.00 (1.38) | 3.00 (1.37) | 2.00 (0.91) |
| Polyethylene Glycol (PEG 8000) | 0 | 1.00 (0.46) | 0 | 0 |
| Polyethylene Glycol (PEG 400) | 0 | 0 | 1.00 (0.46) | 1.00 (0.46) |
| Sodium Lauryl Sulfate | 0 | 0 | 0.13 (0.06) | 0.14 (0.06) |
| Film Coating | | | | |
| Opadry ® Clear | 0 | 0 | 1.09 (0.50) | 1.09 (0.50) |
| Total Coated Tablet Wt. (mg) | 214.01 | 217.00 | 218.22 | 219.23 |

TABLE 1c 60 mg Dextromethorphan HBr Tablet formulations 6 and 7

| Material Name | Tablet 6 mg/tab (% w/w) | Tablet 7 mg/tab (% w/w) |
|---|---|---|
| Core Tablet | | |
| Dextromethorphan HBr | 56.00 (26.02) | 56.00 (26.02) |
| Methocel ™ K4M Premium CR | 20.00 (9.29) | 20.49 (9.52) |
| Methocel ™ K15M Premium CR | 20.00 (9.29) | 20.49 (9.52) |
| Lactose Monohydrate Fast-Flo | 65.17 (30.28) | 64.55 (29.99) |
| MCC PH-102 | 45.28 (21.04) | 44.85 (20.84) |
| Cabosil ® M-5 | 1.02 (0.47) | 1.05 (0.49) |
| Magnesium Stearate | 1.53 (0.71) | 1.57 (0.73) |
| Total Core Tablet Wt. (mg) | 209.00 | 209.00 |
| Active Coating | | |
| Dextromethorphan HBr | 4.00 (1.86) | 4.00 (1.86) |
| Methocel E3 Prem | 0.89 (0.41) | 0.89 (0.41) |
| Povidone K30 | 0.89 (0.41) | 0.89 (0.41) |
| Polyethylene Glycol (PEG 400) | 0.44 (0.20) | 0.44 (0.20) |
| Sodium Lauryl Sulfate | 0.01 (0.004) | 0.01 (0.004) |
| Total Coated Tablet Wt. (mg) | 215.23 | 215.23 |

Example 2: General Procedure for the Preparation of Dextromethorphan HBr Extended Release Tablet (60 mg Strength)

Dextromethorphan HBr, METHOCEL' K4MCR, METHOCEL' K15MCR, lactose monohydrate, microcrystalline cellulose (MCC), and CAB-O-SIL®, are added to a vibratory sifter (ASTM #20) and sifted into an appropriately sized V-shell blender. The resulting sifted mixture is then blended for 8 minutes at 25 RPM. Magnesium stearate is then added to a vibratory sifter (ASTM #20) and added to the mixture contained in the blender. The resulting mixture is then blended for 4 minutes at 25 RPM. The mixture is then transferred to a Manesty Beta-press with B-tooling (0.3380" diameter, round, plain-faced) and pressed into tablets. Exemplary tablet formulations produced by this procedure are provided in Tables 2a, 2b and 2c.

TABLE 2a 60 mg Dextromethorphan HBr Tablet formulations 8-11

| Material Name | Tablet 8 mg/tab (% w/w) | Tablet 9 mg/tab (% w/w) | Tablet 10 mg/tab (% w/w) | Tablet 11 mg/tab (% w/w) |
|---|---|---|---|---|
| Dextromethorphan HBr | 60.00 (28.17) | 60.00 (28.17) | 60.00 (28.17) | 60.00 (28.17) |
| Methocel ™ K4M Premium CR | 20.00 (9.39) | 20.00 (9.39) | 20.00 (9.39) | 30.00 (14.08) |
| Methocel ™ K15M Premium CR | 20.00 (9.39) | 30.00 (14.08) | 40.00 (18.78) | 40.00 (18.78) |
| Lactose Monohydrate Fast-Flo | 65.17 (30.60) | 59.21 (27.80) | 53.29 (25.02) | 47.39 (22.25) |
| MCC PH-102 | 45.28 (21.26) | 41.12 (19.31) | 37.04 (17.39) | 32.94 (15.46) |
| Cabosil ® M-5 | 1.02 (0.48) | 1.07 (0.50) | 1.07 (0.50) | 1.07 (0.50) |
| Magnesium Stearate | 1.53 (0.72) | 1.60 (0.75) | 1.60 (0.75) | 1.60 (0.75) |
| Total Tablet Wt. (mg) | 213.00 | 213.00 | 213.00 | 213.00 |

TABLE 2b 60 mg Dextromethorphan HBr Tablet formulations 12-15

| Material Name | Tablet 12 mg/tab (% w/w) | Tablet 13 mg/tab (% w/w) | Tablet 14 mg/tab (% w/w) | Tablet 15 mg/tab (% w/w) |
|---|---|---|---|---|
| Dextromethorphan HBr | 60.00 (28.17) | 60.00 (25.75) | 60.00 (25.75) | 60.00 (25.00) |
| Methocel ™ K4M Premium CR | 40.00 (18.78) | 40.00 (17.17) | 20.00 (8.58) | 40.00 (16.67) |
| Methocel ™ K15M Premium CR | 40.00 (18.78) | 40.00 (17.17) | 30.00 (12.88) | 40.00 (16.67) |
| Lactose Monohydrate Fast-Flo | 41.51 (19.49) | 41.51 (17.82) | 59.21 (25.41) | 57.00 (23.75) |
| MCC PH-102 | 28.82 (13.53) | 48.82 (20.95) | 61.12 (26.23) | 40.00 (16.67) |
| Cabosil ® M-5 | 1.07 (0.50) | 1.07 (0.46) | 1.07 (0.46) | 1.20 (0.50) |
| Magnesium Stearate | 1.60 (0.75) | 1.60 (0.69) | 1.60 (0.69) | 1.80 (0.75) |
| Total Tablet Wt. (mg) | 213.00 | 233.00 | 233.00 | 240.00 |

TABLE 2c 60 mg Dextromethorphan HBr Tablet formulations 16-19

| Material Name | Tablet 16 mg/tab (% w/w) | Tablet 17 mg/tab (% w/w) | Tablet 18 mg/tab (% w/w) | Tablet 19 mg/tab (% w/w) |
|---|---|---|---|---|
| Dextromethorphan HBr | 60.00 (28.17) | 60.00 (26.67) | 60.00 (26.67) | 60.00 (26.67) |
| Methocel ™ K4M Premium CR | 20.00 (9.39) | 40.00 (17.78) | 20.00 (8.89) | 40.00 (17.78) |
| Methocel ™ K15M Premium CR | 30.00 (14.08) | 40.00 (17.78) | 30.00 (13.33) | 40.00 (17.78) |
| Lactose Monohydrate Fast-Flo | 59.21 (27.80) | 41.51 (18.45) | 59.21 (26.32) | 33.51 (14.89) |
| MCC PH-102 | 41.12 (19.31) | 40.82 (18.14) | 53.12 (23.61) | 48.82 (21.70) |
| Cabosil ® M-5 | 1.07 (0.50) | 1.07 (0.48) | 1.07 (0.48) | 1.07 (0.48) |
| Magnesium Stearate | 1.60 (0.75) | 1.60 (0.71) | 1.60 (0.71) | 1.60 (0.71) |
| Total Tablet Wt. (mg) | 213.00 | 225.00 | 225.00 | 225.00 |

Example 3: General Procedure for the Preparation of Dextromethorphan HBr Extended Release Tablet with (30 mg Strength)

Dextromethorphan HBr, METHOCEL' K4MCR, METHOCEL' K15MCR, Cabosil M-5, lactose monohydrate, and/or microcrystalline cellulose (MCC), and CAB-O-SIL® are added to a vibratory sifter (ASTM #20) and sifted into an appropriately sized V-shell blender. The resulting sifted mixture is then blended for 8 minutes at 25 RPM. Magnesium stearate is then added to an oscillating sifter (ASTM #20) and added to the mixture contained in the blender. The resulting mixture is then blended for 4 minutes at 25 RPM. The mixture is then transferred to a Manesty Beta-press with B-tooling (0.3380" diameter, round, plain-faced) and pressed into 233 mg tablets. Exemplary tablet formulations produced by this procedure are provided in Table 3.

TABLE 3

30 mg Dextromethorphan HBr Tablet formulations 20-23

| Material Name | Tablet 20 mg/tab (% w/w) | Tablet 21 mg/tab (% w/w) | Tablet 22 mg/tab (% w/w) | Tablet 23 mg/tab (% w/w) |
|---|---|---|---|---|
| Dextromethorphan HBr | 30.00 (25.00) | 30.00 (25.00) | 30.00 (25.00) | 30.00 (25.00) |
| Methocel ™ K4M Premium CR | 30.00 (25.00) | 40.00 (33.33) | 20.00 (16.67) | 20.00 (16.67) |
| Methocel ™ K15M Premium CR | 10.00 (8.33) | 0 (0) | 20.00 (16.67) | 20.00 (16.67) |
| Lactose Monohydrate Fast-Flo | 48.80 (40.67) | 48.80 (40.67) | 48.80 (40.67) | 28.80 (24.00) |
| MCC PH-102 | 0 (0) | 0 (0) | 0 (0) | 20.00 (16.67) |
| Cabosil ® M-5 | 0.60 (0.50) | 0.60 (0.50) | 0.60 (0.50) | 0.60 (0.50) |
| Magnesium Stearate | 0.60 (0.50) | 0.60 (0.50) | 0.60 (0.50) | 0.60 (0.50) |
| Total Tablet Wt. (mg) | 120.00 | 120.00 | 120.00 | 120.00 |

Example 4: Preparation of Dextromethorphan HBr Extended Release Tablet with Color Coating (Tablet 24 and Tablet 25, Respectively)

Core Tablet

Dextromethorphan HBr 12.9 kg, METHOCEL' K4MCR 4.29 kg or 8.58 kg, METHOCEL™ K15MCR 6.44 kg or 8.58 kg, CAB-O-SIL® M-5 0.230 kg, lactose monohydrate 12.7 kg or 8.91 kg, and microcrystalline cellulose (MCC) 13.1 kg or 10.5 kg are passed through a Quadro Comil 196 using a 32R mesh screen, round stator and mill speed of 500 rpm (range: 300-600 rpm). The materials are then transferred to 5 ft³ V-shell blender and then blended for 15 minutes at 22 RPM. Magnesium stearate 0.343 kg is then added to the mixture contained in the same blender, and the mixture blended for 5 minutes at 22 RPM. The mixture is then transferred to a Manesty Unipress B-tooling (0.3380" diameter, round, "DX" on one side, "12" on the other side) and pressed into 233 mg tablets.

Opadry Color Coating:

Purified water 11.9 kg is mixed with OPADRY® Orange 2.10 kg using an overhead mixer for 45 minutes and sprayed onto the coated tablets described above using a Compulab 24" Pan with 60100 nozzles, 134255-45 aircaps, 2 spray system 7310-1/4 Jauco SS, 8 o'clock gun position, and 7 inch nozzle distance for tablet bed. Target outlet temperature of 45° C. (range: 35-55° C., air flow of 900 cfm (range: 800-1000 cfm), atomization air pressure of 45 psi (range: 30-60 psi), pan speed of 9 rpm (range: 6-12 rpm), and spray rate of 180 g/min (range: 120-210 g/min).

Exemplary tablet formulations produced by this procedure are provided in Table 4.

TABLE 4

60 mg Dextromethorphan HBr Tablet formulations 24 and 25 (color film coating)

| Material Name | Tablet 24 mg/tab (% w/w) | Tablet 25 mg/tab (% w/w) |
| --- | --- | --- |
| Dextromethorphan HBr | 60.00 (25.00) | 60.00 (25.00) |
| Methocel ™ K4M Premium CR | 20.00 (8.33) | 40.00 (16.67) |
| Methocel ™ K15M Premium CR | 30.00 (12.50) | 40.00 (16.67) |
| Lactose Monohydrate Fast-Flo | 59.21 (24.67) | 41.51 (17.30) |
| MCC PH-102 | 61.12 (25.47) | 48.82 (20.34) |
| Cabosil ® M-5 | 1.07 (0.45) | 1.07 (0.45) |
| Magnesium Stearate | 1.60 (0.67) | 1.60 (0.67) |
| Film Coating | | |
| Opadry ® II Orange 47B130006 | 6.99 (2.91) | 6.99 (2.91) |
| Total | 240.00 | 240.00 |

Figure 2:
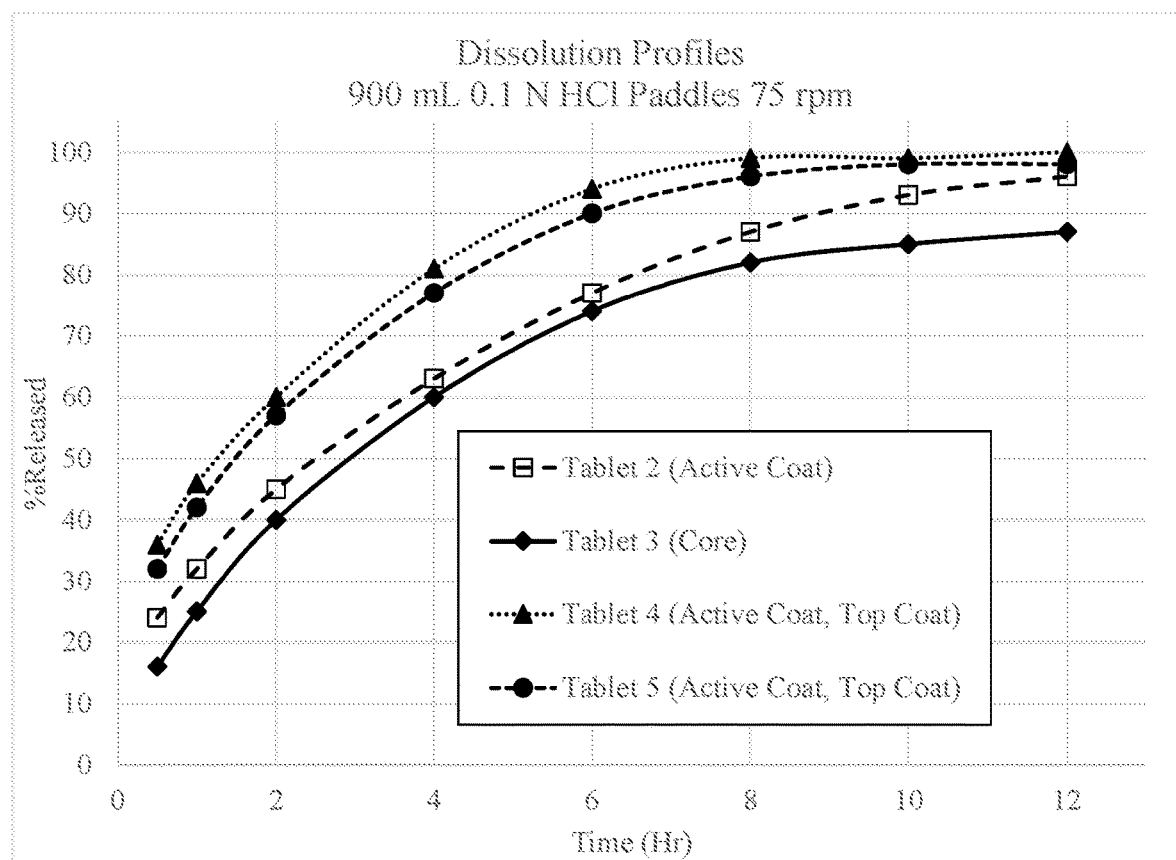
FIG. 2 is a line graph providing the dissolution profile of tablet formulations 2, 3, 4, and 5 of the present invention, each having 51 mg of dextromethorphan HBr in the core tablet and 9 mg of dextromethorphan HBr in the active coating.
Figure 3:
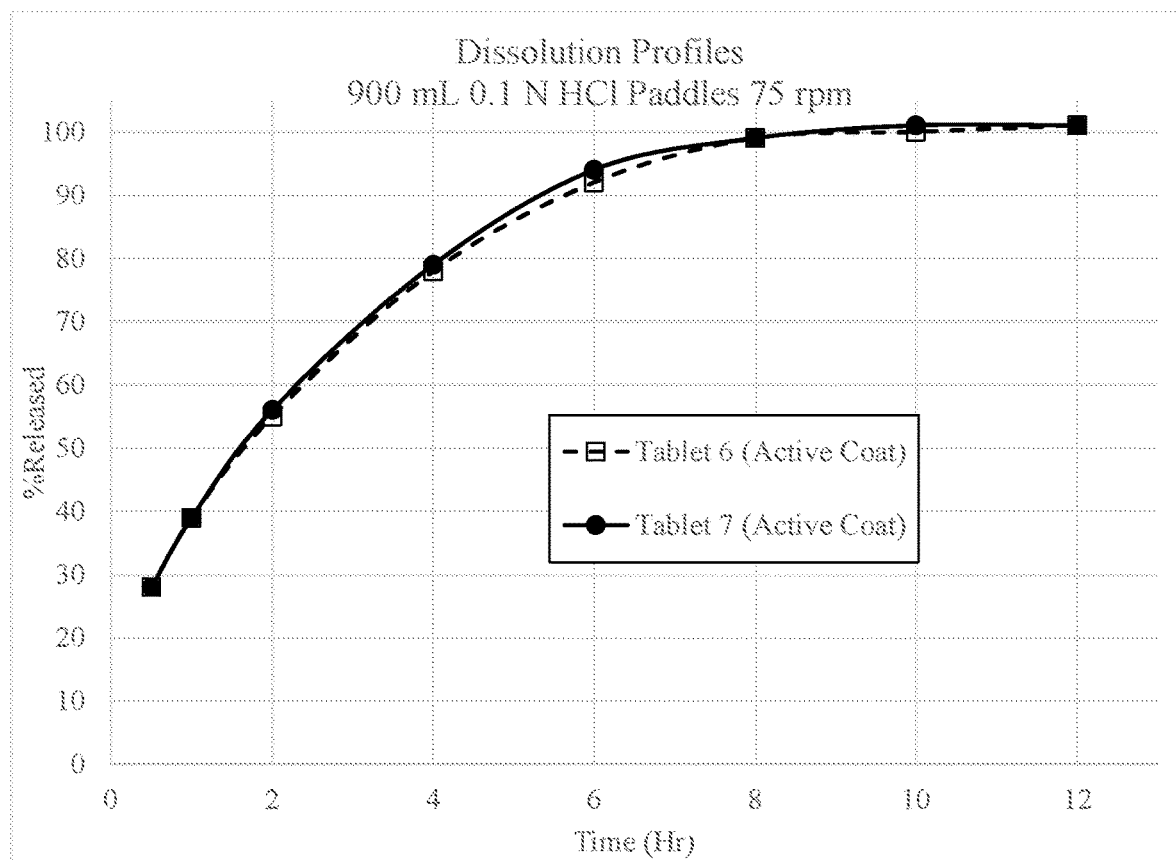
FIG. 3 is a line graph providing the dissolution profile of tablet formulations 6 and 7 of the present invention, each having 56 mg dextromethorphan HBr in the core tablet and 4 mg of dextromethorphan HBr in the active coating.
Figure 4:
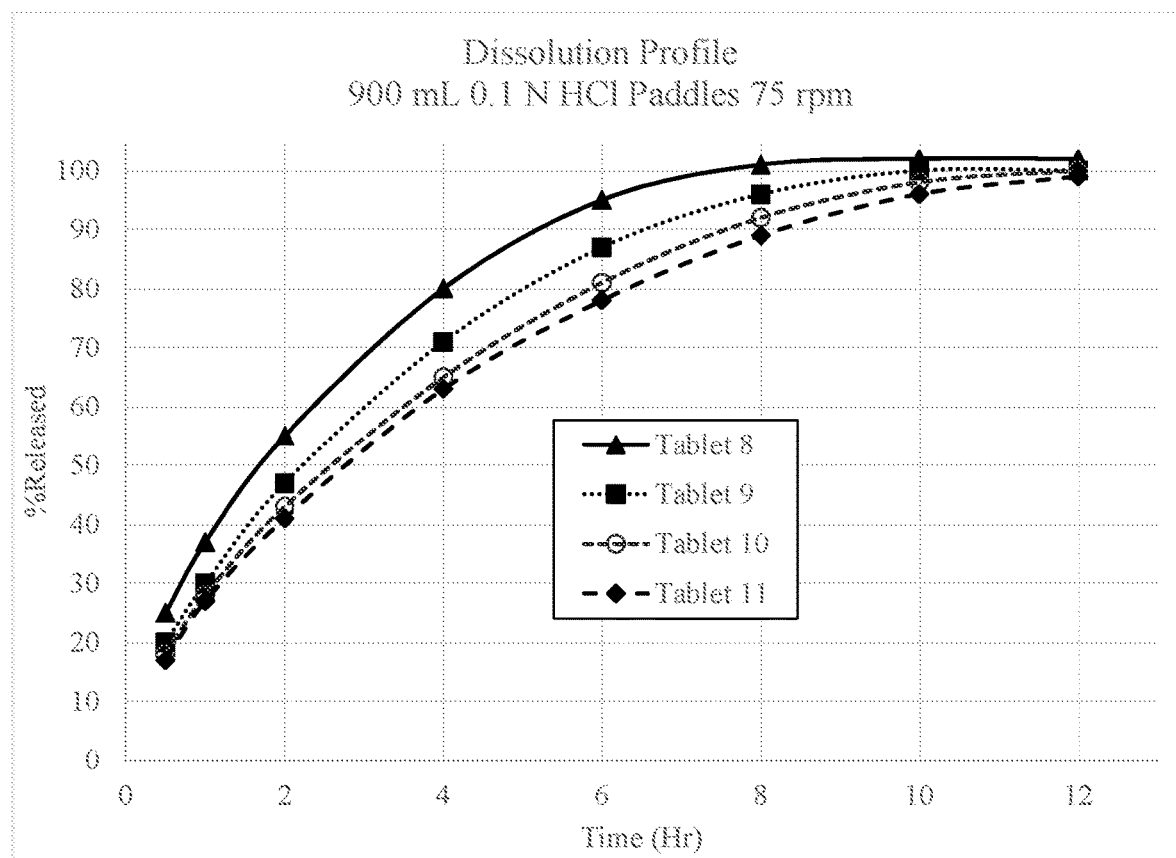
FIG. 4 is a line graph providing the dissolution profile of tablet formulations 8, 9, 10, and 11 of the present invention, each having 60 mg of dextromethorphan HBr in the core tablet, different amounts of controlled release agents and no active coating.
Figure 5:
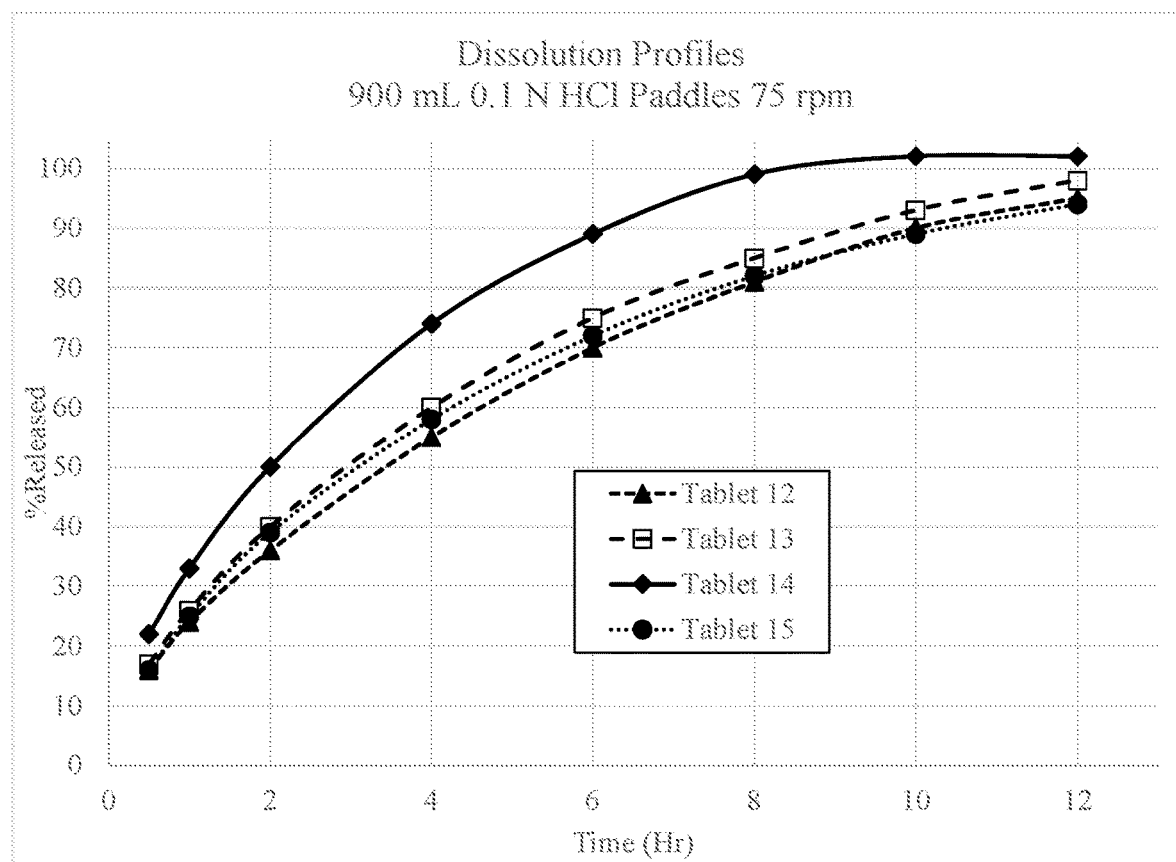
FIG. 5 is a line graph providing the dissolution profile of tablet formulations 12, 13, 14, and 15 of the present invention, each having 60 mg of dextromethorphan HBr in the core tablet, different amounts of controlled release agents and no active coating.
Figure 6:
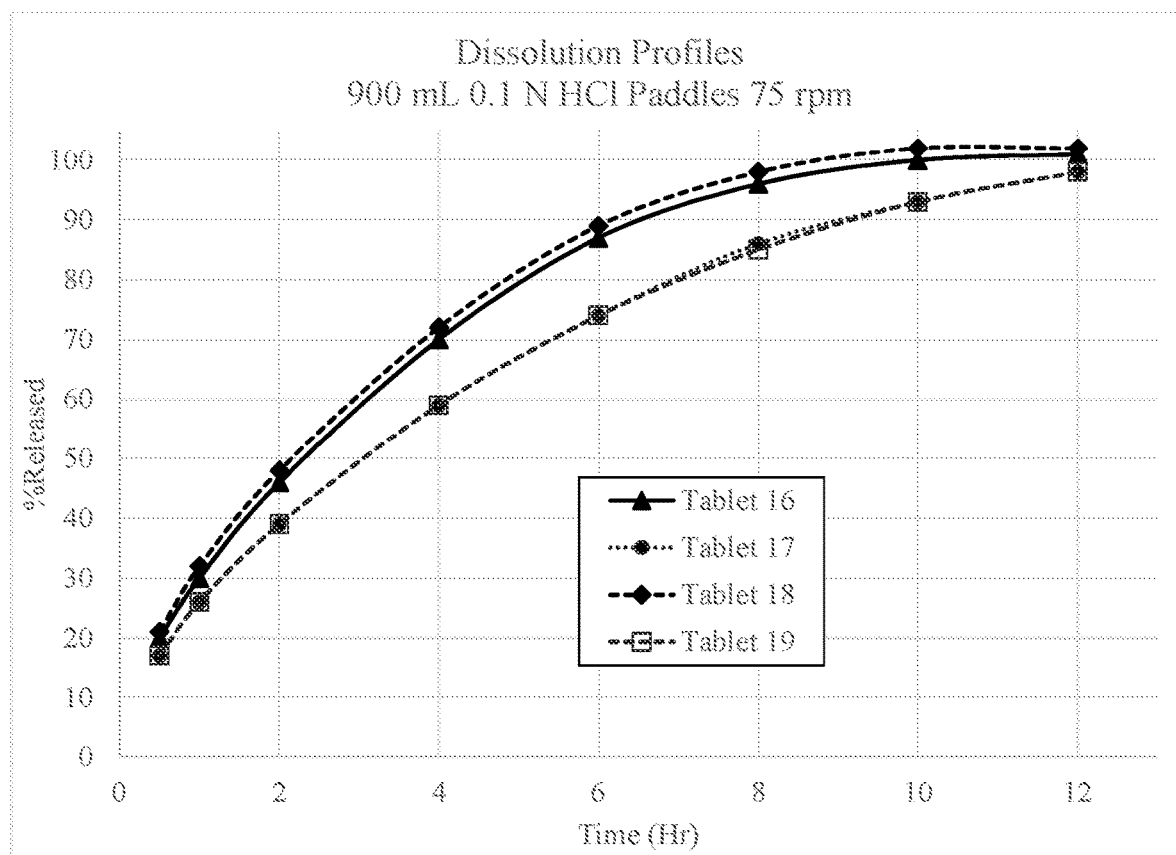
FIG. 6 is a line graph providing the dissolution profile of tablet formulations 16, 17, 18, and 19 of the present invention, each having 60 mg of dextromethorphan HBr in the core tablet, different amounts of controlled release agents and no active coating.
Figure 7:
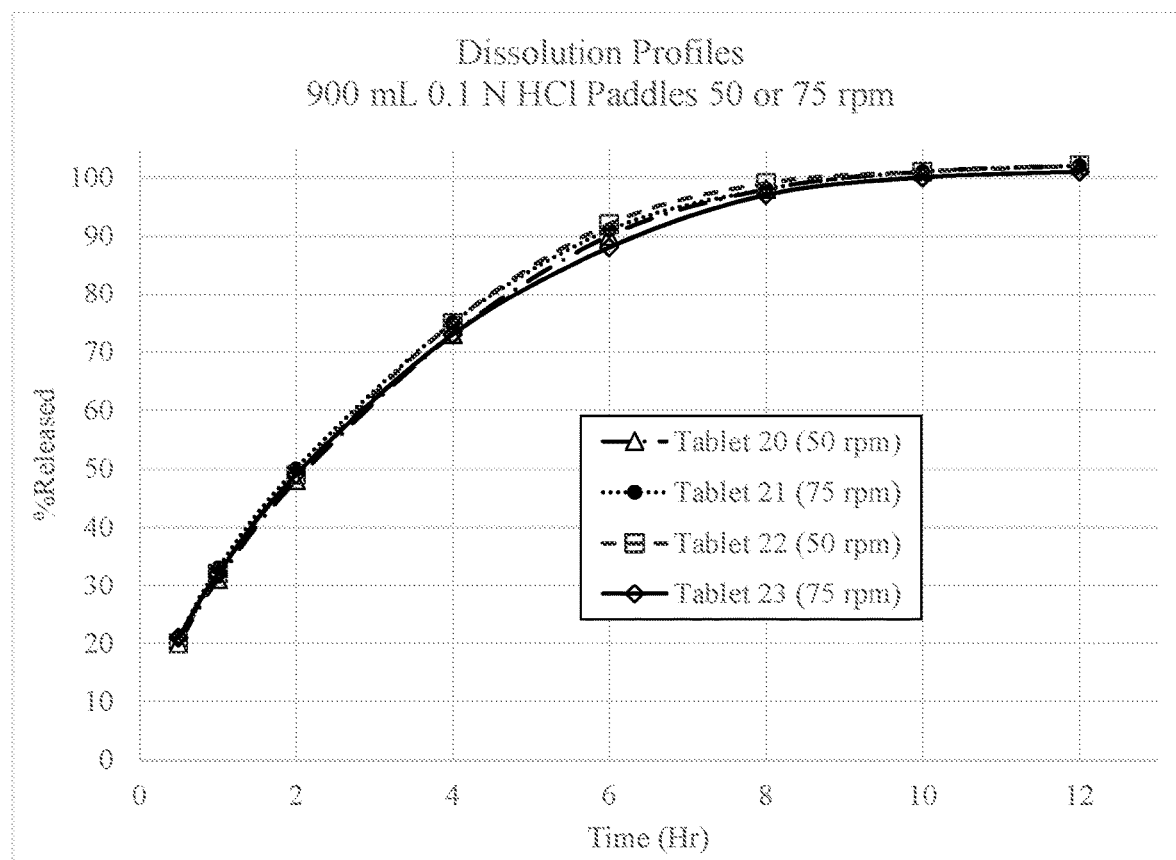
FIG. 7 is a line graph providing the dissolution profile of tablet formulations 20, 21, 22, and 23 of the present invention, each having 30 mg dextromethorphan HBr and no active coating.
Figure 8:
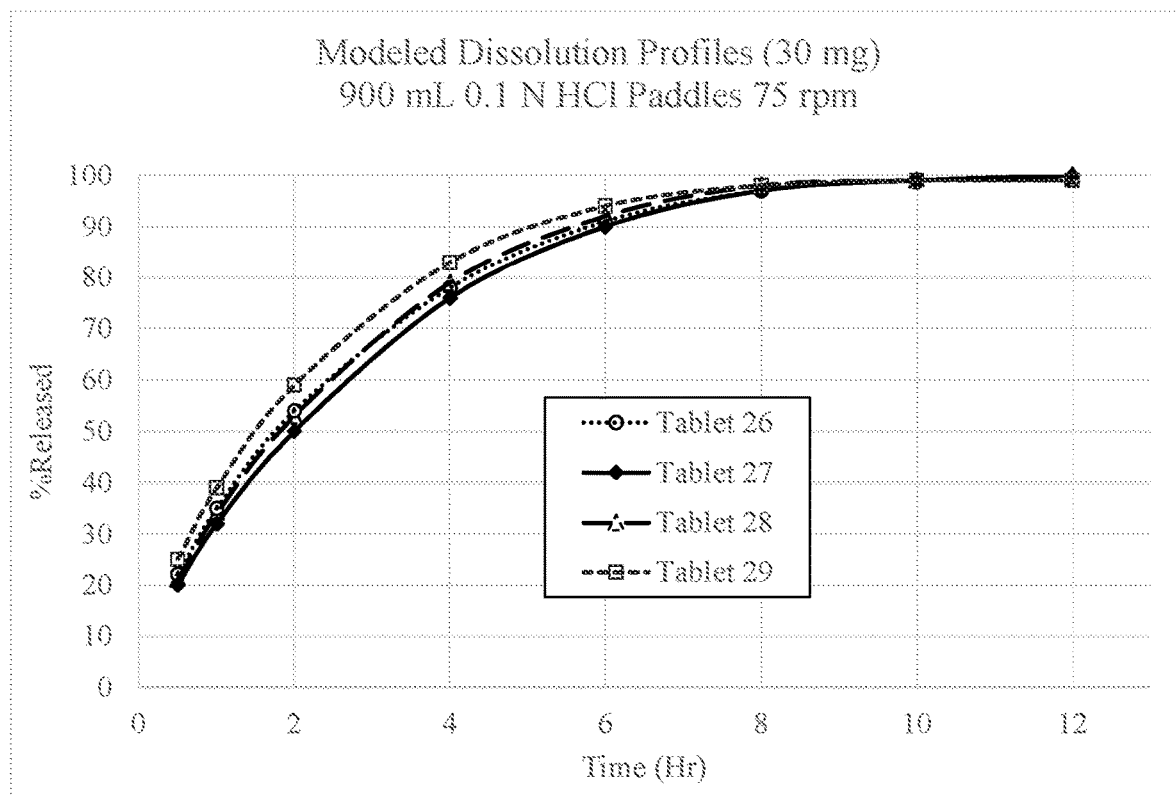
FIG. 8 is a line graph providing the modeled dissolution profile of tablet formulations 26, 27, 28, and 29 of the present invention, each having 30 mg dextromethorphan HBr and no active coating.
Figure 9:
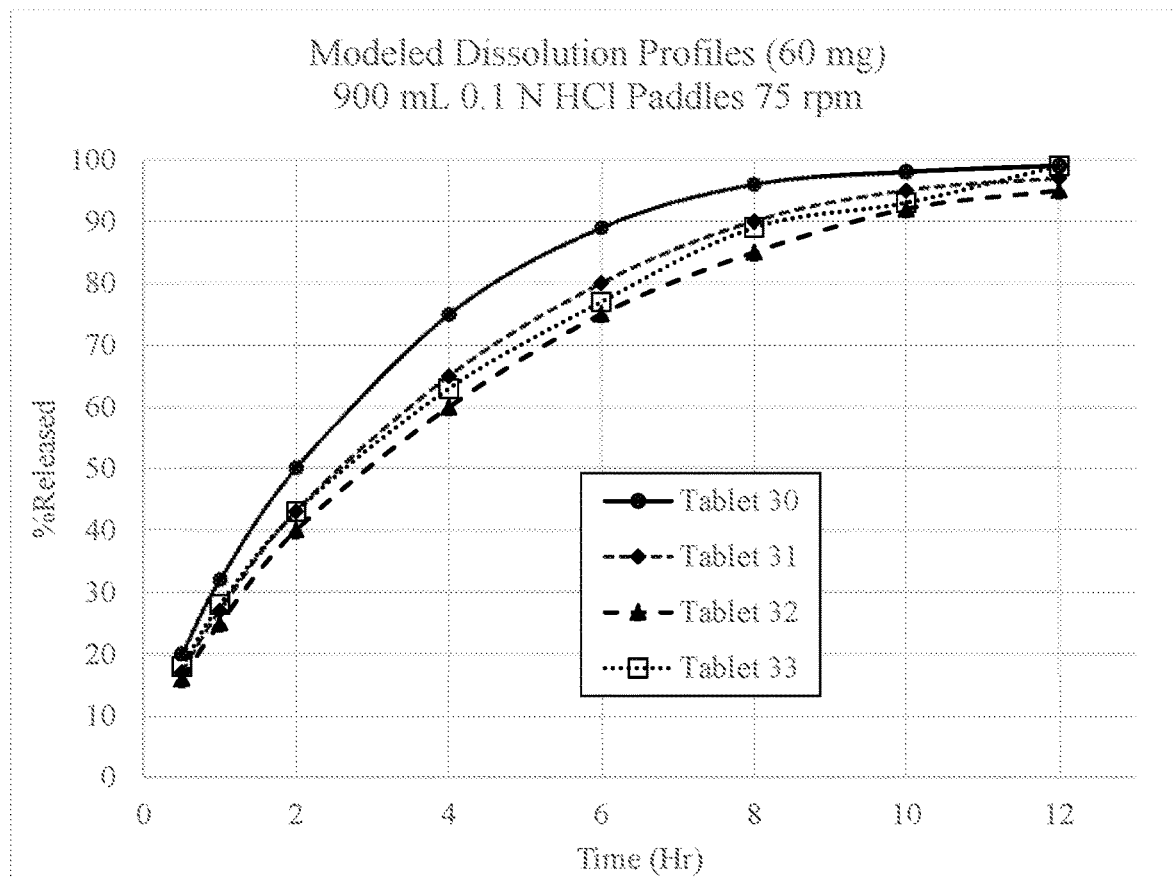
FIG. 9 is a line graph providing the modeled dissolution profile of tablet formulations 30, 31, 32, and 33 of the present invention, each having 60 mg dextromethorphan HBr and no active coating.

Example 5: General Procedure for the Determination of the Dissolution Rate of the Tablet Compositions of the Invention The dissolution rates of the tablet formulations of the invention were determined using a USP Apparatus II dissolution bath, with 900 mL of degassed 0.1 N HCl Dissolution Medium at 37.0±0.5° C. in each vessel, with the paddles rotating at 75 rpm. In any given experiment, a single tablet is dropped into each dissolution vessel. A sampling should be performed at the 0.5, 1, 2, 4, 6, 8, 10 and 12 hour time points. At each pull, 10 mL should be sampled and filtered through a 0.45 μm Whatman PP filter, discarding the first 5 mL of filtrate before collecting the analytical sample. The concentration of dextromethorphan in each aliquot was then determined by UPLC, and then normalized to determine the % released. The current marketed sustained release suspension, Delsym®, is a resin-based complex with a dissolution profile showing incomplete release of about 60% in 12 hours in 900 mL, 0.1 N HCl, USP Apparatus II, 75 rpm. The proposed product shows complete release from the tablet in 12 hours in 900 mL, 0.1 N HCl, USP Apparatus II, 75 rpm. The proposed product releases dextromethorphan or a pharmaceutically acceptable salt thereof from the tablet at less than 40% in 30 minutes, between 15 and 60% in 1 hour, between 25% and 75% in 2 hours, between 40% and 90% in 4 hours and more than 70% in 8 hours, in 900 mL, 0.1 N HCl, USP Apparatus II, 75 rpm. Dissolution profiles under these dissolution conditions for Tablet formulations 1-25 are provided in FIGS. 1-9.

Example 6. Dissolution Modeling for Additional Formulation Compositions

During the development of new pharmaceutical dosage forms the main concern is to develop robust formulation which can provide constant bioavailability and therapy to the patient. To provide guidance for successful drug development and post market monitoring, in vitro dissolution testing has emerged as a preferred method of choice to evaluate new formulations. Dissolution may be defined as the amount of drug substance that goes into solution per unit time under standardized conditions of liquid/solid interface. Dissolution tests measure in vitro drug release as a function of time, and can be considered an indicator of all phenomena that lead to the release of API into a solution. Dissolution tests are performed with drug products to elucidate drug release mechanism, stability, the robustness of the manufacturing process, and predict in vivo behavior of dosage form. Development of optimal dissolution conditions and suitable formulations is a tedious job and may warrant significant and exhaustive resources. In addition, to improve the data collected from dissolution conditions and provide meaningful in vitro and in vivo correlation/relation (IVIVC/R), and in order to have better understanding the impact of formulation and process variables of different formulations on drug release and to establish IVIVC/R, an in vitro simulation model was developed using commercially available simulation software called, DDDPlus™ (Dose Disintegration and Dissolution Plus) from Simulation Plus, Inc.

DDDPlus™ is a computer program that models and simulates the in vitro dissolution of various pharmaceutical dosage forms. DDDPlus™ simulation is essentially the numerical integration of a set of differential equations that coordinate well-characterized physical actions that occur during dissolution. During the simulation program DDDPlus™ will account for the following three major variables: 1) formulation components physicochemical characteristics, 2) certain formulation process characteristics and 3) dissolution test conditions. The program is organized into three sections—Formulation Variables, Dissolution Method, and Simulation. It is required to incorporate different variables to predict either drug release of a given formula composition or predict a formula composition for a target dissolution profile.

For Dextromethorphan HBr Extended Release (ER) tablets, USP II dissolution apparatus at 75 rpm in 900 mL 0.1 N HCl, dissolution conditions were selected to develop the simulation model with default DDDPlus™ software parameters to predict various formula compositions. Dextromethorphan HBr ER tablets DDDPlus™ model was validated by comparing the predicted dissolution results from the simulation model with observed dissolution results. Simulation model is considered suitable when predictive error (% PE) is within 10% internal validation and 15% of external validation when compared with observed results. The validated simulation model was used to predict the dissolution profiles of various formulation compositions and tablet physical characteristics. The same model was utilized to predict various formula compositions to yield desired dissolution profiles. Dissolution data for Tablet formulations 26-33 are provided in Tables 6 and 7.

TABLE 6

30 mg strength tablet compositions and dissolution modeling

| Material Name | Tablet 26 mg/tab (% w/w) | Tablet 27 mg/tab (% w/w) | Tablet 28 mg/tab (% w/w) | Tablet 29 mg/tab (% w/w) |
|---|---|---|---|---|
| Dextromethorphan HBr | 30.00 (12.50) | 30.00 (25.00) | 30.00 (17.44) | 30.00 (25.00) |
| Methocel ™ K4M Premium CR | 40.00 (16.67) | 20.00 (16.67) | 30.00 (17.44) | 33.00 (27.50) |
| Methocel ™ K15M Premium CR | 40.00 (16.67) | 20.00 (16.67) | 30.00 (17.44) | — |
| Lactose Monohydrate Fast-Flo | 56.51 (23.55) | 20.76 (17.30) | 47.70 (27.73) | 27.90 (23.25) |
| MCC PH-102 | 63.82 (26.59) | 24.41 (20.34) | 33.10 (19.24) | 27.90 (23.25) |
| Cabosil ® M-5 | 1.07 (0.45) | 0.54 (0.45) | 0.60 (0.35) | 0.60 (0.50) |
| Magnesium Stearate | 1.60 (0.67) | 0.80 (0.67) | 0.60 (0.35) | 0.60 (0.50) |
| Film Coating | | | | |
| Opadry ® II Orange 47B130006 | 6.99 (2.91) | 3.50 (2.91) | — | — |
| Total | 240.00 | 120.00 | 172.00 | 120.00 |

| | Time (hours) | % Released | | | |
|---|---|---|---|---|---|
| Dissolution Data | 0.5 | 22 | 20 | 21 | 25 |
| | 1 | 35 | 32 | 34 | 39 |
| | 2 | 54 | 50 | 53 | 59 |
| | 4 | 78 | 76 | 79 | 83 |
| | 6 | 91 | 90 | 92 | 94 |
| | 8 | 97 | 97 | 98 | 98 |
| | 10 | 99 | 99 | 99 | 99 |
| | 12 | 99 | 100 | 100 | 99 |

TABLE 7

60 mg strength tablet compositions and dissolution modeling

| Material Name | Tablet 30 mg/tab (% w/w) | Tablet 31 mg/tab (% w/w) | Tablet 32 mg/tab (% w/w) | Tablet 33 mg/tab (% w/w) |
|---|---|---|---|---|
| Dextromethorphan HBr | 60.00 (18.40) | 60.00 (18.40) | 60.00 (18.40) | 60.00 (25.75) |
| Methocel ™ K4M Premium CR | 40.00 (12.27) | 60.00 (18.40) | 73.00 (22.39) | 79.00 (33.91) |
| Methocel ™ K15M Premium CR | 40.00 (12.27) | 60.00 (18.40) | 75.00 (23.01) | — |
| Lactose Monohydrate Fast-Flo | 84.33 (25.87) | 77.46 (23.76) | 56.19 (17.24) | 45.67 (19.60) |
| MCC PH-102 | 99.00 (30.37) | 65.87 (20.21) | 59.14 (17.22) | 45.66 (19.60) |
| Cabosil ® M-5 | 1.07 (0.33) | 1.07 (0.33) | 1.07 (0.33) | 1.07 (0.46) |
| Magnesium Stearate | 1.60 (0.49) | 1.60 (0.49) | 1.60 (0.49) | 1.60 (0.69) |
| Film Coating | | | | |
| Opadry ® II Orange 47B130006 | — | — | — | — |
| Total | 326.00 | 326.00 | 326.00 | 233.00 |

| | Time (hours) | % Released | | | |
|---|---|---|---|---|---|
| Dissolution Data | 0.5 | 20 | 17 | 16 | 18 |
| | 1 | 32 | 27 | 25 | 28 |
| | 2 | 50 | 43 | 40 | 43 |
| | 4 | 75 | 65 | 60 | 63 |
| | 6 | 89 | 80 | 75 | 77 |
| | 8 | 96 | 90 | 85 | 89 |
| | 10 | 98 | 95 | 92 | 93 |
| | 12 | 99 | 97 | 95 | 99 |

Example 7: Bioavailability Studies (Tablets 1, 24, and 25)

Open-label, balanced, randomized, single oral dose, bioequivalence studies of Dextromethorphan Hydrobromide Extended Release tablets 60 mg (Tablet 1, Tablet 24 or Tablet 25) with Delsym® 30 mg/5 mL (Dextromethorphan Polistirex) extended-release suspension in a dose of 60 mg/10 mL among healthy, adult, human male and/or female study participants under fasting conditions were performed.

Table 7 below provides the Geometric Means Ratios (GMR) of Test to Reference for Cmax, $AUC_{0-T}$ and $AUC_{0-inf}$ for Dextromethorphan.

TABLE 7

Bioavailability Study Examples: Summary of in vivo results for Dextromethorphan HBr Extended Release tablets compared to Delsym ® extended release suspension

| TEST vs. RLD | $C_{max}$ | $AUC_{0-T}$ | $AUC_{0-inf}$ |
|---|---|---|---|
| 60 mg ER Tablet (with active coating) (Tablet 1)/Delsym | 135.18 | 115.24 | 108.17 |
| 60 mg ER Tablet (with no active coating) (Tablet 24)/Delsym | 118.20 | 115.16 | 112.35 |
| 60 mg ER Tablet (with no active coating) (Tablet 25)/Delsym | 104.90 | 114.52 | 116.40 |

OTHER EMBODIMENTS

The foregoing disclosure has been described in some detail by way of illustration and example, for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

What is claimed is:

1. A sustained release pharmaceutical tablet composition comprising:
  a) a core tablet sustained release formulation comprising
    i. dextromethorphan HBr in an amount selected from about 12.50%, 17.44%, 18.40%, 23.26%, 23.28%, 23.37%, 23.50%, 23.83%, 25.00%, 25.75%, 26.02%, 26.67%, and 28.17% by weight of the composition;
    ii. hydroxypropyl methylcellulose having an apparent viscosity of from about 2,663 to about 4,970 mPa·s at 2 wt % in water, a methyl substitution between about 22.0% and 24.0%, and a hydroxypropyl substitution between about 7.5% and 9.5%, in an amount selected from the group consisting of about 8.33%, 8.58%, 8.89%, 9.12%, 9.13%, 9.17%, 9.22%, 9.29%, 9.39%, 9.52%, 12.27%, 14.08%, 15.89%, 16.67%, 17.17%, 17.44%, 17.78%, 18.40%, 18.78%, 22.39%, 25.00%, 27.50%, 33.33%, and 33.91% by weight of the composition;
    iii. hydroxypropyl methylcellulose having an apparent viscosity of from about 13,275 to about 24,780 mPa·s, a methyl substitution between about 22.0% and 24.0%, and a hydroxypropyl substitution between about 8.5% and 10.5%, in an amount selected from the group consisting of about 8.33%, 9.12%, 9.13%, 9.17%, 9.29%, 9.39%, 9.52%, 12.22%, 12.50%, 12.88%, 13.33%, 14.08%, 15.67%, 15.89%, 16.67%, 17.17%, 17.44%, 17.78%, 18.40%, 18.78%, and 23.01% by weight of the composition;
    iv. lactose monohydrate in an amount selected from about 14.89%, 17.24%, 17.30%, 17.82%, 18.45%, 19.49%, 19.60%, 22.25%, 22.64%, 23.25%, 23.55%, 23.75%, 23.76%, 24.00%, 24.67%, 25.02%, 25.41%, 25.87%, 26.23%, 26.32%, 27.73%, 27.80%, 29.73%, 29.74%, 29.86%, 29.99%, 30.28%, 30.60%, and 40.67% by weight of the composition;
    v. microcrystalline cellulose in an amount selected from about 0%, 13.53%, 15.46%, 15.89%, 16.67%, 17.22%, 17.39%, 18.14%, 18.22%, 19.24%, 19.31%, 19.60%, 20.21%, 20.34%, 20.65%, 20.67%, 20.75%, 20.84%, 20.95%, 21.04%, 21.26%, 21.70%, 23.25%, 23.61%, 25.47%, 26.23%, 26.59%, and 30.37% by weight of the composition;
    vi. fumed silica in an amount selected from about 0.33%, 0.35%, 0.45%, 0.46%, 0.47%, 0.48%, 0.49%, or 0.50% by weight of the composition; and
    vii. magnesium stearate in an amount selected from about 0.35%, 0.49%, 0.50%, 0.67%, 0.69%, 0.70%, 0.71%, 0.72%, 0.73%, and 0.75% by weight of the composition;
  b) optionally, an active coating comprising:
    i. dextromethorphan or a pharmaceutically acceptable salt thereof in an amount selected from about 1.86%, 4.11%, 4.12%, 4.15%, and 4.21% by weight of the composition;
    ii. hydroxypropyl methylcellulose having an apparent viscosity range of about 2.4-7 mPa·s at 2 wt % in water, a methyl substitution range of about 28.0%-30.0%, and a hydroxypropyl substitution range of about 7.0%-12.0% in an amount selected from about 0%, 0.41%, 0.47%, and 0.91% by weight of the composition;
    iii. polyvinyl pyrrolidone in an amount selected from about 0%, 0.41%, 0.91%, 1.37%, and 1.38% by weight of the composition;
    iv. sodium lauryl sulfate in an amount selected from about 0%, 0.004%, 0.01%, and 0.06% by weight of the composition;
    v. PEG 400 or PEG 8000 in an amount selected from about 0%, 0.20%, and 0.46% by weight of the composition;
  and c) the film coating is absent or comprises a polymer and a plasticizer;
  wherein the tablet has a volume of from about 0.0063 in$^3$ to about 0.0183 in$^3$, a surface area of from about 0.194 in$^2$ to about 0.395 in$^2$, and a surface area to volume ratio of from about 19.4 in$^{-1}$ to about 31.0 in$^{-1}$.

2. The sustained release pharmaceutical tablet composition of claim 1, wherein
  a) the core tablet sustained release formulation comprises
    i. about 23.28% of dextromethorphan HBr by weight of the composition;
    ii. about 9.13% of hydroxypropyl methylcellulose having an apparent viscosity of from about 2,663 to about 4,970 mPa·s at 2 wt % in water, a methyl substitution between about 22.0% and 24.0%, and a hydroxypropyl substitution between about 7.5% and 9.5%, by weight of the composition;

iii. about 9.13% of hydroxypropyl methylcellulose having an apparent viscosity of from about 13,275 to about 24,780 mPa·s, a methyl substitution between about 22.0% and 24.0%, and a hydroxypropyl substitution between about 8.5% and 10.5%, by weight of the composition;
iv. about 29.74% of lactose monohydrate by weight of the composition;
v. about 20.67% microcrystalline cellulose by weight of the composition;
vi. about 0.47% fumed silica by weight of the composition; and
vii. about 0.70% magnesium stearate by weight of the composition;
b) the active coating is present and comprises
i. about 4.11% dextromethorphan HBr by weight of the composition;
ii. about 0.91% polyvinylpyrrolidone by weight of the composition;
iii. about 0.91% of hydroxypropyl methylcellulose having an apparent viscosity range of 2.4-3.6 mPa·s, a methyl substitution of 28.0%-30.0% (inclusive), and a hydroxypropyl substitution of 7.0%-12.0% (inclusive) by weight of the composition;
iv. about 0.46% of polyethylene glycol by weight of the composition; and
v. about 0.01% of sodium lauryl sulfate by weight of the composition; and
c) the film coating is present and comprises a polymer, plasticizer and pigment.

3. The pharmaceutical composition of claim 2, comprising a film coating in an amount of about 0.50% by weight of the composition, wherein the film coating comprises hypromellose, polyethylene glycol, and optionally, one or more of polydextrose, talc, a pigment, and titanium dioxide.

4. The sustained release pharmaceutical tablet composition of claim 1, wherein
a) the core tablet sustained release formulation comprises
i. about 25.00% of dextromethorphan HBr by weight of the composition;
ii. about 8.33% of hydroxypropyl methylcellulose having an apparent viscosity of from about 2,663 to about 4,970 mPa·s at 2 wt % in water, a methyl substitution between about 22.0% and 24.0%, and a hydroxypropyl substitution between about 7.5% and 9.5%, by weight of the composition;
iii. about 12.50% of hydroxypropyl methylcellulose having an apparent viscosity of from about 13,275 to about 24,780 mPa·s, a methyl substitution between about 22.0% and 24.0%, and a hydroxypropyl substitution between about 8.5% and 10.5%, by weight of the composition;
iv. about 24.67% of lactose monohydrate by weight of the composition;
v. about 25.47% microcrystalline cellulose by weight of the composition;
vi. about 0.45% fumed silica by weight of the composition; and
vii. about 0.67% magnesium stearate by weight of the composition;
or,
the core tablet sustained release formulation comprises
i. about 25.00% of dextromethorphan HBr by weight of the composition;
ii. about 16.67% of hydroxypropyl methylcellulose having an apparent viscosity of from about 2,663 to about 4,970 mPa·s at 2 wt % in water, a methyl substitution between about 22.0% and 24.0%, and a hydroxypropyl substitution between about 7.5% and 9.5%, by weight of the composition;
iii. about 16.67% of hydroxypropyl methylcellulose having an apparent viscosity of from about 13,275 to about 24,780 mPa·s, a methyl substitution between about 22.0% and 24.0%, and a hydroxypropyl substitution between about 8.5% and 10.5%, by weight of the composition;
iv. about 17.30% of lactose monohydrate by weight of the composition;
v. about 20.34% microcrystalline cellulose by weight of the composition;
vi. about 0.45% fumed silica by weight of the composition; and
vii. about 0.67% magnesium stearate by weight of the composition;
b) the active coating is absent; and
c) the film coating comprises a polymer, plasticizer and pigment.

5. The pharmaceutical composition of claim 4, wherein the film coating comprises hypromellose, polyethylene glycol, and optionally, one or more of polydextrose, talc, a pigment, and titanium dioxide, the pharmaceutical composition comprises the film coating in an amount of about 2.91% by weight of the composition, and the total weight of the tablet is about 240 mg.

6. The pharmaceutical composition of claim 1, wherein the active coating further comprises a polyvinyl alcohol—polyethylene glycol copolymer, wherein the polyvinyl alcohol—polyethylene glycol copolymer has an average molecular weight of about 45,000 daltons, and comprises about 75% polyvinyl alcohol units and about 25% polyethylene glycol units by weight, and the active coating and film coating each independently optionally further comprise a flavoring agent, cooling agent, sweetener, or salivation agent.

7. The pharmaceutical composition of claim 1, wherein the tablet has a mass of from about 200 mg to about 326 mg, a volume of from about 0.0106 in$^3$ to about 0.0183 in$^3$, a surface area of from about 0.252 in$^2$ to about 0.395 in$^2$, and a surface area to volume ratio of from about 19.4 in$^{-1}$ to about 23.9 in$^{-1}$.

8. The pharmaceutical composition of claim 7, wherein the tablet has a mass selected from about 213 mg, about 214 mg, about 215 mg, about 217 mg, about 218 mg, about 219 mg, about 225 mg, about 233 mg, about 240 mg, and about 326 mg.

9. The pharmaceutical composition of claim 1, wherein the tablet has a mass of from about 110 mg to about 172 mg, a volume of from about 0.0063 in$^3$ to about 0.0088 in$^3$, a surface area of from about 0.194 in$^2$ to about 0.229 in$^2$, and a surface area to volume ratio of from about 26.2 in$^{-1}$ to about 31.0 in$^{-1}$.

10. The pharmaceutical composition of claim 9, wherein the tablet has a mass selected from about 120 mg, about 172 mg and about 240 mg.

11. The pharmaceutical composition of claim 1, wherein the total amount of dextromethorphan or a pharmaceutically acceptable salt thereof is about 30 mg or about 60 mg.

12. The sustained release pharmaceutical tablet composition according to claim 1
wherein the dextromethorphan or a pharmaceutically acceptable salt thereof is released from the tablet, when the tablet is stirred at 75 rpm, in 900 mL of 0.1 N HCl, and at 37° C.±0.5° C., at i. less than 40% in 30 minutes;
ii. between 15 and 60% in 1 hour;
iii. between 25 and 75% in 2 hours;
iv. between 40 and 90% in 4 hours; and
v. more than 70% in 8 hours.

13. A method of treating cough in a patient in need thereof, comprising administering to a patient in need thereof a pharmaceutical composition according to claim 1.

\* \* \* \* \*